US009932579B2

(12) United States Patent
Paldi et al.

(10) Patent No.: US 9,932,579 B2
(45) **Date of Patent: *Apr. 3, 2018**

(54) PREVENTION AND TREATMENT OF NOSEMA DISEASE IN BEES

(71) Applicant: Beeologics Inc., St. Louis, MO (US)

(72) Inventors: Nitzan Paldi, Moshav Bar Giora (IL); Eitan Glick, Nes Ziona (IL)

(73) Assignee: BEEOLOGICS INC, St. Louis, MO (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/474,205

(22) Filed: Sep. 1, 2014

(65) Prior Publication Data

US 2014/0371298 A1 Dec. 18, 2014

Related U.S. Application Data

(63) Continuation of application No. 13/318,636, filed as application No. PCT/IB2010/051980 on May 5, 2010, now Pat. No. 8,822,426.

(60) Provisional application No. 61/213,086, filed on May 5, 2009.

(51) Int. Cl.

| | |
|---|---|
| ***C12N 15/11*** | (2006.01) |
| ***C07H 21/02*** | (2006.01) |
| ***A01K 51/00*** | (2006.01) |
| ***C12N 15/113*** | (2010.01) |
| ***A61K 31/00*** | (2006.01) |
| ***A61K 31/7088*** | (2006.01) |
| ***A61D 7/00*** | (2006.01) |

(52) U.S. Cl.

CPC .............. *C12N 15/113* (2013.01); *A61D 7/00* (2013.01); *A61K 31/00* (2013.01); *A61K 31/7088* (2013.01); *C12N 2310/11* (2013.01); *C12N 2310/14* (2013.01)

(58) Field of Classification Search

None

See application file for complete search history.

(56) References Cited

U.S. PATENT DOCUMENTS

| | | | |
|---|---|---|---|
| 4,732,250 | A | 3/1988 | Maucher et al. |
| 5,898,031 | A | 4/1999 | Crooke |
| 6,107,094 | A | 8/2000 | Crooke |
| 6,506,559 | B1 | 1/2003 | Fire et al. |
| 7,056,704 | B2 | 6/2006 | Tuschl et al. |
| 7,078,196 | B2 | 7/2006 | Tuschl et al. |
| 8,097,712 | B2 | 1/2012 | Paldi et al. |
| 8,507,457 | B2 | 8/2013 | Paldi et al. |
| 2002/0086356 | A1 | 7/2002 | Tuschl et al. |
| 2003/0044443 | A1 | 3/2003 | Erickson, Jr. et al. |
| 2003/0092651 | A1 | 5/2003 | Norris et al. |
| 2003/0180945 | A1 | 9/2003 | Wang et al. |
| 2004/0259247 | A1 | 12/2004 | Tuschl et al. |
| 2005/0080032 | A1 | 4/2005 | Gross et al. |
| 2005/0095199 | A1 | 5/2005 | Whyard et al. |
| 2007/0219151 | A1 | 9/2007 | Satishchandran et al. |
| 2007/0232188 | A1 | 10/2007 | Probasco |
| 2008/0194512 | A1 | 8/2008 | John et al. |
| 2008/0261303 | A1 | 10/2008 | Kreutzer et al. |
| 2009/0118214 | A1 | 5/2009 | Paldi et al. |
| 2012/0053231 | A1 | 3/2012 | Paldi et al. |
| 2012/0108497 | A1 | 5/2012 | Paldi et al. |
| 2012/0258646 | A1 | 10/2012 | Sela et al. |
| 2013/0289097 | A1 | 10/2013 | Paldi et al. |

FOREIGN PATENT DOCUMENTS

| | | |
|---|---|---|
| AU | 2008325989 | 5/2009 |
| CN | 1505504 | 6/2004 |
| CN | 101139607 | 3/2008 |
| EP | 1416049 | 5/2004 |
| EP | 2 703 490 A1 | 3/2014 |
| EP | 2703489 | 3/2014 |
| EP | 2706114 | 3/2014 |
| WO | WO 97/47193 | 12/1997 |
| WO | WO 99/32619 | 7/1999 |
| WO | WO 00/04176 | 1/2000 |
| WO | WO 01/34815 | 5/2001 |
| WO | WO 2009/060429 | 5/2009 |
| WO | WO 2010/128465 | 11/2010 |
| WO | WO 2011/045796 | 4/2011 |
| WO | WO 2013/153553 | 10/2013 |

OTHER PUBLICATIONS

Advisory Action Before the Filing of an Appeal Brief dated Feb. 22, 2013 from the US Patent and Trademark Office Re. U.S. Appl. No. 13/332,430.

Applicant-Initiated Interview Summary dated Mar. 5, 2013 from the US Patent and Trademark Office Re. U.S. Appl. No. 13/332,430.

Communication Pursuant to Article 94(3) EPC dated Feb. 5, 2015 from the European Patent Office Re. Application No. 13156183.9.

Communication Pursuant to Article 94(3) EPC dated Feb. 6, 2015 from the European Patent Office Re. Application No. 10719620.6.

Communication Pursuant to Article 94(3) EPC dated Nov. 10, 2014 from the European Patent Office Re. Application No. 10779855.5.

Communication Pursuant to Article 94(3) EPC dated Jul. 12, 2013 from the European Patent Office Re. Application No. 08847971.2.

Communication Pursuant to Article 94(3) EPC dated Feb. 17, 2011 from the European Patent Office Re. Application No. 08847971.2.

Communication Pursuant to Article 94(3) EPC dated Feb. 17, 2014 from the European Patent Office Re. Application No. 08847971.2.

Communication Pursuant to Article 94(3) EPC dated Jun. 29, 2012 from the European Patent Office Re. Application No. 08847971.2.

Communication Pursuant to Article 94(3) EPC dated Sep. 29, 2014 from the European Patent Office Re. Application No. 13156180.4.

Communication Pursuant to Article 94(3) EPC dated Sep. 29, 2014 from the European Patent Office Re. Application No. 13156180.5.

Communication Relating to the Results of the Partial International Search dated May 13, 2009 from the International Searching Authority Re.: Application No. PCT/IL2008/001440.

(Continued)

*Primary Examiner* — Richard A Schnizer

(74) *Attorney, Agent, or Firm* — Amanda Carmany-Rampey; David Marsh; Arnold & Porter

(57) ABSTRACT

Compositions and methods for reducing susceptibility and enhancing tolerance to *Nosema* disease (Nosemosis) using RNA interference technology, and more particularly, prevention and treatment of *Nosema* infections in honeybees by feeding of *Nosema*-specific dsRNA.

11 Claims, 11 Drawing Sheets
(11 of 11 Drawing Sheet(s) Filed in Color)

(56) References Cited

OTHER PUBLICATIONS

Communication Relating to the Results of the Partial International Search dated Jul. 24, 2013 from the International Searching Authority Re. Application No. PCT/2013/050321.
European Search Report and the European Search Opinion dated Feb. 3, 2014 from the European Patent Office Re. Application No. 13156180.4.
European Search Report and the European Search Opinion dated Feb. 3, 2014 from the European Patent Office Re. Application No. 13156180.5.
Examination Report dated May 12, 2014 From the Instituto Mexicano de la Propiedad Industrial Re. Application No. MX/a/2012/004378 and Its Translation Into English.
Examination Report dated Jan. 30, 2015 From the Instituto Mexicano de la Propiedad Industrial Re. Application No. MX/a/2012/004378 and Its Translation Into English.
Examination Report dated Oct. 31, 2013 From the Instituto Mexicano de la Propiedad Industrial Re. Application No. MX/a/2012/004378 and Its Summary in English.
International Preliminary Report on Patentability dated Feb. 1, 2010 from the International Preliminary Examining Authority Re.: Application No. PCT/IL2008/001440.
International Preliminary Report on Patentability dated Nov. 17, 2011 From the International Bureau of WIPO Re. Application No. PCT/IB2010/051980.
International Preliminary Report on Patentability dated Oct. 2014 From the International Bureau of WIPO Re. Application No. PCT/IL2013/050321.
International Preliminary Report on Patentability dated Apr. 26, 2012 From the International Bureau of WIPO Re. Application No. PCT/IL2010/000844.
International Search Report and the Written Opinion dated Jul. 19, 2010 From the International Searching Authority Re. Application No. PCT/IB2010/051980.
International Search Report and the Written Opinion dated Feb. 24, 2011 From the International Searching Authority Re. Application No. PCT/IL2010/000844.
International Search Report and the Written Opinion dated Oct. 28, 2013 From the International Searching Authority Re. Application No. PCT/IL2013/050321.
International Search Report and the Written Opinion dated Nov. 30, 2010 From the International Searching Authority Re. Application No. PCT/IB2010/053776.
Office Action dated Dec. 18, 2014 From the Israel Patent Office Re. Application No. 216154.
Office Action dated Jan. 19, 2014 From the Israel Patent Office Re. Application No. 205594 and Its Translation Into English.
Office Action dated Mar. 19, 2012 From the Israel Patent Office Re. Application No. 205594 and Its Translation Into English.
Office Action dated Jan. 26, 2015 From the Israel Patent Office Re. Application No. 219193.
Office Action dated Dec. 31, 2014 From the Israel Patent Office Re. Application No. 205594.
Official Action dated Jun. 28, 2010 From the US Patent and Trademark Office Re. U.S. Appl. No. 12/222,949.
Patent Examination Report dated Oct. 23, 2013 From the Australian Government, IP Australia Re. Application No. 2008325989.
Patent Examination Report dated Nov. 6, 2014 From the Australian Government, IP Australia Re. Application No. 2010244122.
Restriction Official Action dated Nov. 21, 2012 From the US Patent and Trademark Office Re. U.S. Appl. No. 13/318,636.
Translation dated Feb. 9, 2015 of Office Action dated Jan. 26, 2015 From the Israel Patent Office Re. Application No. 219193.
Translation dated Jan. 15, 2015 of Office Action dated Dec. 18, 2014 From the Israel Patent Office Re. Application No. 216154.
Translation dated Jan. 20, 2015 of Office Action dated Dec. 31, 2014 From the Israel Patent Office Re. Application No. 205594.
Translation of Office Action dated Jul. 2, 2013 From the State Intellectual Property Office of the People's Republic of China Re. Application No. 201080056585.9.
Written Opinion dated Aug. 13, 2009 From the International Searching Authority Re. Application No. PCT/IL2008/001440.
Akiyoshi et al. "Genomic Survey of the Non-Cultivatable Opportunistic Human Pathogen, Enterocytozoon Bieneusi", PLoS Pathogens, 5(1): e1000261: 1-10, Jan. 2009.
Amdam et al. "Altered Physiology in Worker Honey Bees (Hymenoptera: Apidae) Infested With the Mite Varroa Destructor (Acari: Varroidae): A Factor in Colony Loss During Overwintering?", Journal of Economic Entomology, 97(3): 741-747, 2004.
Amdam et al. "The Hive Bee to Forager Transition in Honeybee Colonies: The Double Repressor Hypothesis", Journal of Theoretical Biology, 223: 451-464, 2003.
Aronstein et al. "SID-I Is Implicated in Systemic Gene Silencing in the Honey Bee", Journal of Agricultural Research and Bee World, XP009115329, 45(1): 20-24, Jan. 2006.
Baum et al. "Control of Coleopteran Insect Pests Through RNA Interference", Nature Biotechnology, 25(11): 1322-1326, Nov. 2007, Advance Online Publication, Nov. 4, 2007.
Burri et al. "Microsporidian Mitosomes Retain Elements of the General Mitochondrial Targeting System", Proc. Natl. Acad. Sci. USA, 103(43): 15916-15920, Oct. 24, 2006.
Campbell et al. "Gene-Knockdown in the Honey Bee Mite Varroa Destructor by a Non-Invasive Approach: Studies on a Glutathione S-Transferase", Parasites & Vectors, XP002621493, 3(73): 1-10, Aug. 16, 2010. Abstract, Figs.4, 6, Table 1.
Carthew "Gene Silencing by Double-Stranded RNA", Current Opinion in Cell Biology, XP002263320, 13: 244-248, 2001.
Chawla-Sarkar et al. "Downregulation of Bcl-2, FLIP or IAPs (XIAP and Survivin) by SiRNAs Sensitizes Resistant Melanoma Cells to APO2L/TRAIL-Induced Apoptosis", Cell Death and Differentiation, 11: 915-923, Apr. 30, 2004.
Chen et al. "High Throughput Genome-Wide Survey of Small RNAs From the Parasitic Protists Giardia Intestinalis and Trichomonas Vaginalis", Genome, Biology and Evolution, p. 165-175, Jul. 6, 2009.
Chen et al. "Nosema Ceranae Is a Long-Present and Wide-Spread Microsporidian Infection of the European Honey Bee (*Apis mellifera*) in the United States", Journal of Invertebrate Pathology, XP022438643, 97(2): 186-188, Jan. 29, 2008.
Cornman et al. "Genomic Analyses of the Microsporidian Nosema Ceranae, An Emergent Pathogen of Honey Bees", PLoS Pathogens, 5(6): e1000466: 1-14, Jun. 2009.
Cox-Foster et al. "A Metagenomic Survey of Microbes in Honey Bee Colony Collapse Disorder", Science, 318(5848): 283-287, Oct. 2007.
Cox-Foster et al. "A Metagenomic Survey of Microbes in Honey Bee Colony Collapse Disorder", Science, XP002533680, 318(5848): 283-287, Oct. 2007.
Cox-Foster et al. "Saving the Honeybee. The Mysterious Ailment Called Colony Collapse Disorder Has Wiped Out Large Numbers of the Bees That Pollinate a Third of Our Crops", Scientific American, p. 40-47, Apr. 2009.
De La Fuente et al. "RNA Interference for the Study and Genetic Manipulation of Ticks", Trends in Parasitology, 23(9): 427-433, Sep. 2007. Abstract.
Di Prisco et al. "Varroa Destructor Is an Effective Vector of Israeli Acute Paralysis Virus in the Honeybee, *Apis mellifera*", Journal of General Virology, 92: 151-155, 2011.
Dietemann et al. "Varroa Destructor: Research Avenues Towards Sustainable Control", Journal of Apicultural Research, XP055069108, 51(1): 125-132, Feb. 2012.
Fairbairn et al. "Host-Delivered RNAi: An Effective Strategy to Silence Genes in Plant Parasitic Nematodes", Planta, 226(6): 1525-1533, Nov. 2007. Abstract.
Franco Nunes et al. "A Non-Invasive Method for Silencing Gene Transcription in Honeybees Maintained Under Natural Conditions", Insect Biochemistry and Molecular Biology, XP002523702, 39(2): 157-160, Feb. 2009.
Garbian et al. "Bidirectional Transfer of RNAi Between Honey Bee and Varroa Destructor: Varroa Gene Silencing Reduces Varroa Population", PLOS Pathogens, XP055069058, 8(12): e1003035-1-e1003035-9, Dec. 20, 2012.

(56) References Cited

OTHER PUBLICATIONS

Gill et al. "Stripped-Down DNA Repair in a High Reduced Parasite", BMC Molecular Biology, 8(24): 1-14, Mar. 20, 2007.
Henderson et al. "U.S. National Bee Colony Loss Survey, www.beesurvey.com, Preliminary Findings With Respect to Colony Collapse Disorder (CCD)", Bee Alert Technology, Inc., Mar. 26, 2007.
Hunter et al. "Large-Scale Field Application of RNAi Technology Reducing Israeli Acute Paralysis Virus Disease in Honey Bees (Apis mellifera, Hymenoptera: Apidae)", PLoS Pathogens, 6(12): e1001160-1-e1001160-10, Dec. 2010.
Katinka et al. "Genome Sequence and Gene Compaction of the Eukaryote Parasite Encephalitozoon Cuniculi", Nature, 414(6862): 450-453, Nov. 22, 2001. Abstract.
Liu et al. "Effect of a Fluvalinate-Resistance-Associated Sodium Chennel Mutation from Varroa Mites on Cockroach Sodium Channel Sensitivity to Fluvalinate, A Pyrethroid Insecticide", Insect Biochemistry and Molecular Biology, XP025014535, 36(11): 885-889, Nov. 1, 2006. Abstract.
Liu et al. "Prevention of Chinese Sacbrood Virus Infection in Apis Cerana Using RNA Interference", Current Microbiology, 61(5): 422-428, Nov. 2010. Abstract.
Maggi et al. "Resistance Phenomena to Amitraz From Population of the Ectoparasitic Mite Varroa Destructor of Argentina", Parasitology Research, 107(5): 1189-1192, Oct. 2010. Abstract.
Malhotra et al. "Double-Stranded RNA-Mediated Gene Silencing of Cysteine Proteases (Falcipain-1 and -2) of Plasmodium Falciparum", Molecular Mcirobiology, 45(5): 1245-1254, 2002.
Malone et al. "Effects of Transgene Products on Honey Bees (Apis mellifera) and Bumblebees (Bombus Sp.)", Apidologie, XP009141014, 32(4): 287-304, Jul. 2001. p. 288, 1-h Col., § 3-p. 289, 1-h Col., § 2.
Maori et al. "IAPV, A Bee-Affecting Virus Associated With Colony Collapse Disorder Can Be Silenced by DsRNA Ingestion", Insect Molecular Biology, XP002523701, 18(1): 55-60, Feb. 2009. Abstract.
Maori et al. "'Israel Acute Paralysis Virus of Bees, Complete Genome", GenBank EMBL, EBI Dbfetch, XP002533679, Accession No. EF219380, Nov. 21, 2007.
Maori et al. "Reciprocal Sequence Exchange Between Non-Retro Viruses and IIosts Leading to the Appearance of New IIost Phenotypes", Virology, XP022065066, 362(2): 342-349, May 5, 2007.
Mayack et al. "Energetic Stress in the Honeybee Apis mellifera from Nosema Ceranae Infection", Journal of Invertebrate Pathology, 100(3): 185-188, Mar. 2009.
Mutti et al. "IRS and TOR Nutrient-Signaling Pathways Act Via Juvenile Hormone to Influence Honey Bee Caste Fate", Journal of Experimental Biology, 214(Pt.23): 3977-3984, Dec. 1, 2011. Abstract.
Nakayashiki et al. "Evolution and Diversification of RNA Silencing Proteins in Fungi", Journal of Molecular Evolution, 63(1): 127-135, Jul. 2006.
Nielsen et al. "Sacbrood Virus Isolate T73/05A Polyprotein Gene, Partial CDs", Database EMBL [Online], XP002719130, Retrieved From IBIS, Database Accession No. EF570887, May 12, 2007.
O'Riordan et al. "Inhibitor of Apoptosis (IAP) Proteins in Eukaryotic Evolution and Development: A Model of Thematic Conservation", Developmental Cell, 15(4): 497-508, Oct. 2008.
Palacios et al. "Genetic Analysis of Israel Acute Paralysis Virus: Distinct Clusters Are Circulating in the United States", Journal of Virology, 82(13): 6209-6217, Jul. 2008.
Palacios et al. "Israel Acute Paralysis Virus of Bees Strain OZ6-AUSTRALIA-2007, Complete Genome", Database EMBL [Online], XP002533681, Retrieved From EBI, Database Accession No. EU436456, Jun. 19, 2008.
Paldi et al. "Effective Gene Silencing in a Microsporidian Parasite Associated With Honeybee (Apis mellifera) Colony Declines", Applied and Environmental Microbiology, 76(17): 5960-5964, Sep. 2010.
Patel et al. "The Making of a Queen: TOR Pathway Is a Key Player in Diphenic Caste Development", PLoS ONE, 2(6): e509-1-e509-7, Jun. 2007.
Price et al. "RNAi-Mediated Crop Protection Against Insects", Trends in Biotechnology, XP022757296, 26(7): 393-400, Jul. 2008.
Robalino et al. "Double-Stranded RNA and Antiviral Immunity in Marine Shrimp: Inducible IIost Mechanisms and Evidence for the Evolution of Viral Counter-Responses", Developmental & Comparative Immunology, 31: 539-547, 2007.
Siomi et al. "On the Road to Reading the RNA-Interference Code", Nature, 457(7228): 396-404, Jan. 22, 2009. Abstract.
Slamovits et al. "Genome Compaction and Stability in Microsporidian Intracellular Parasites", Current Biology, 14(10): 891-896, May 25, 2004.
Standifer "Honey Bee Nutrition and Supplemental Feeding", Beekeeping in the United States Agriculture Handbook, 335: 39-45, Oct. 1980.
Steeves et al. "Transgenic Soybeans Expressing SiRNAs Specific to a Major Sperm Protein Gene Suppress Heterodera Glycines Reproduction", Functional Plant Biology, 33(11): 991-999, Nov. 1, 2006. Abstract.
Taylor et al. "Validation of Spermidine Synthase as a Drug Target in African Trypanosomes", Biochemical Journal, 409(2): 563-569, Jan. 15, 2008.
Tsaousis et al. "A Novel Route for ATP Acquisition by the Remnant Mitochondria of Encephalitozoon Cuniculi", Nature, 453(7194): May 22, 2008. Abstract.
Ullu et al. "RNA Interference in Protozoan Parasites", Cellular Microbiology, 6(6): 509-519, 2004.
Van Engelsdorp "Colony Collapse Disorder: A Descriptive Study", PLoS One, 4(8): e6481: 1-17, 2009.
Wang et al. "Molecular Characterization of an Arachnid Sodium Channel Gene From the Varroa Mite (Varroa Destructor)", Insect Biochemistry and Molecular Biology, XP002621492, 33(7): 733-739, Jul. 2003. Abstract.
Whitfield et al. "BB170006B20C05.5 Bee Brain Normalized/Subtracted Library, BB17 Apis mellifera cDNA Clone BB170006B20C05 5', mRNA Sequence", Database EMBL [Online], XP002719131, Retrieved IBIS, Database Accession No. BI503250, Aug. 30, 2001.
Williams "Unique Physiology of Host-Parasite Interactions in Microsporidia Infections", Cellular Microbiology, XP002589428, 11(11): 1551-1560, Nov. 2009.
Williams et al. "Genome Sequence Surveys of Brachiola Algerae and Edhazardia Aedis Reveal Micriosporidia With Low Gene Densities", BMC Genomics, 9(200): 1-9, Apr. 29, 2008.
Yadav et al. "Host-Generated Double Stranded RNA Induces RNAi in Plant-Parasitic Nematodes and Protects the Host From Infection", Molecular & Biochemical Parasitology, 148: 219-222, 2006.
Zhou et al. "The Effects of Brood Comb Cell Size on the Reproductive Behavior of the Ectoparasitic Mite Varroa Destructor on Honey Bees", Chinese Jurnal of Entomology, 43(1): 89-93, Dec. 31, 2006, Abstract only.
Examination Report dated Mar. 20, 2015 From the Government of India, Patent Office, Intellectual Property Building Re. Application No. 1150/MUMNP/2010.
Communication Pursuant to Article 94(3) EPC dated Jun. 8, 2015 From the European Patent Office Re. Application No. 13156185.4.
Communication Under Rule 164(2)(a) EPC dated Oct. 21, 2015 From the European Patent Office Re. Application No. 13723252.6.
Office Action dated Dec. 21, 2015 From the Israel Patent Office Re. Application No. 240416 and Its Translation Into English.
Lanzi et al. "Deforming Wing Virus Gene for Polyprotein, Genomic RNA", NCBI Database [Online], GenBank Accession No. AJ489744.2, Database Accession No. AJ489744, May 12, 2006.
Leat et al. "Black Queen Cell Virus Nonstructural Polyprotein (ORF1) and Structural Polyprotein (ORF2) Genes, Complete Cds", Database NCBI [Online], GenBank Accession No. AF183905.1, Database Accession No. AF183905, Aug. 16, 2000.
Rangeshwaran et al. "Sacbrood Virus Isolate 1110 Polyprotein Gene, Complete Cds", NCBI Database [Online], GenBank Accession No. JX194121.1, Database Accession No. JX194121, Aug. 27, 2013.

(56) References Cited

OTHER PUBLICATIONS

Requisition by the Examiner and Examination Search Report dated Mar. 19, 2015 From the Canadian Intellectual Property Office Re. Application No. 2,704,858.
Shen et al. "The Role of Varroa Mites in Infections of Kashmir Bee Virus (KBV) and Deformed Wing Virus (DWV) in Honey Bees", Virology, 342: 141-149, Available Online Aug. 18, 2005.
Communication Pursuant to Article 94(3) EPC dated Sep. 1, 2015 From the European Patent Office Re. Application No. 10779855.5.
Communication Pursuant to Article 94(3) EPC dated Sep. 4, 2015 From the European Patent Office Re. Application No. 13156183.9.
Decision on Rejection dated Aug. 3, 2015 From the State Intellectual Property Office of the People's Republic of China Re. Application No. 201080056585.9 and Its Translation Into English.
Communication Pursuant to Article 94(3) EPC dated May 29, 2015 From the European Patent Office Re. Application No. 13156180.4.
Extended European Search Report dated Feb. 6, 2014, in European Patent Application No. 13156183.9.
Final Office Action dated Aug. 1, 2013, in U.S. Appl. No. 13/318,636.
Final Office Action dated Mar. 18, 2011, in U.S. Appl. No. 12/222,949.
Final Office Action dated Oct. 15, 2012, in U.S. Appl. No. 13/332,430.
International Preliminary Report on Patentability dated Feb. 21, 2012, in International Application No. PCT/IB2010/053776.
International Search Report dated Aug. 13, 2009, in International Application No. PCT/IL2008/001440.
Maori et al., "Isolation and characterization of Israeli acute paralysis virus, a dicistrovirus affecting honeybees in Israel: evidence for diversity due to intra- and inter-species recombination," *Journal of General Virology*, 88:3428-3438 (2007).
Non-Final Office Action dated Apr. 15, 2014, in U.S. Appl. No. 13/446,557.
Non-Final Office Action dated Feb. 5, 2014, in U.S. Appl. No. 13/446,557.
Non-Final Office Action dated Jan. 7, 2013, in U.S. Appl. No. 13/318,636.
Non-Final Office Action dated May 30, 2012, in U.S. Appl. No. 13/332,430.
Non-Final Office Action dated May 4, 2015, in U.S. Appl. No. 13/932,051.
Non-Final Office Action dated Sep. 23, 2010, in U.S. Appl. No. 12/222,949.
Peyretaillade et al., "Microsporidian *Encephalitozoon cuniculi*, a unicellular eukaryote with an unusual chromosomal dispersion of ribosomal genes and a LSU rRNA reduced to the universal core," *Nucleic Acids Research*, 26(15):3513-3520 (1998).
Second Office Action dated May 12, 2014, in Chinese Patent Application No. 201080056585.9.
Third Office Action dated Nov. 25, 2014, in Chinese Patent Application No. 201080056585.9.
Boutros et al., Genome-Wide RNAi Analysis of Growth and Viability in Drosophila Cells, 2003. Science. 303:832-835.
Dietzl et al. A genome-wide transgenic RNAi library for conditional gene inactivation in Drosophila. 2007. Nature. 448:151-157.
Lee et al. A systematic RNAi screen identifies a critical role for mitochondria in C. elegans longevity. 2003. Nature Genetics. 33:40-48.
Examination Report dated Aug. 25, 2015 From the Intellectual Property Office of New Zealand Re. Application No. 700791.
Official Action dated Sep. 28, 2015 From the US Patent and Trademark Office Re. U.S. Appl. No. 13/932,051.

PREVENTION AND TREATMENT OF NOSEMA DISEASE IN BEES

RELATED APPLICATIONS

This application is a continuation of U.S. patent application Ser. No. 13/318,636 filed on Nov. 3, 2011, which is a National Phase of PCT Patent Application No. PCT/IB2010/051980 having International filing date of May 5, 2010, which claims the benefit of priority of U.S. Provisional Patent Application No. 61/213,086 filed on May 5, 2009. The contents of the above applications are all incorporated by reference as if fully set forth herein in their entirety.

SEQUENCE LISTING STATEMENT

The ASCII file, entitled 60245SequenceListing.txt, created on Aug. 13, 2014, comprising 50,913.275 bytes, submitted concurrently with the filing of this application is incorporated herein by reference.

FIELD OF THE INVENTION

The invention relates to compositions and methods for reducing susceptibility to *Nosema* spp infection in bees and more particularly, to the use of composition for reduction of *Nosema* mitosomial gene expression for prevention and treatment of *Nosema* spp in honeybees.

BACKGROUND

The importance of honeybees and other pollinating insects to the global world economy far surpasses their contribution in terms of honey production. The United States Department of Agriculture (USDA) estimates that every third bite we consume in our diet is dependent on a honeybee to pollinate that food. The total contribution of pollination in terms of added value to fruit crops exceeds $15 billion per annum, with indirect potential consequence of $75 billion dollars.

Microsporidia are basal fungi and obligate intracellular parasites of other eukaryotes characterized by extreme genomic and cellular reduction. Two described species of microsporidia, *Nosema apis* and *Nosema ceranae*, cause a widespread and destructive disease in adult honey bee. *Nosema* disease is widespread across the world, and it has been observed that *nosema* pathogenesis, together with increased viral load, are the best predictors of weak and collapsing colonies. In Europe, disappearing colony syndrome has been directly attributed to *Nosema ceranae*, and the risk of colony depopulation is six times higher in colonies infected with *N. ceranae* than in uninfected ones. Recently, it was shown that natural *Nosema ceranae* infection can cause the sudden collapse of bee colonies.

Transmission of *Nosema* in honey bee colonies is mainly via the fecal-oral route in which pathogens are spread from diseased hosts to uninfected hosts via ingestion of nucleated *Nosema* spores from fecal material from infected bees. The spores geminate within the midgut and release polar tubes that transfer their sporoplasm into midgut epithelial cells. Inside the cell, the sporoplasm grows to form a multinuclear *plasmodium*, or "meront", replicating to generate more spores, usually numbering in the millions per infected bee.

Current Anti-*Nosema* Protocol: Fumagillin

Fumagillin is an antibiotic derived from the fungus *Aspergillus* fumigates. It is an anti-angiogenic agent that covalently and selectively binds and inhibits the methionine aminopeptidase, MetAP-2 and has been used for many years to treat microsporidiosis caused by *Nosema* in honeybees. It is used extensively in the United States where beekeepers drench their hives in sucrose solution containing Fumagillin. However, Fumagillin does not kill *Nosema* spores, and has rapidly deteriorating potency after application, resulting in only partial and temporary anti-*Nosema* effect, since new bees emerge constantly in a colony, and re-application is required several times a year. Indeed, differences between treated and untreated colonies disappear several months after treatment, with several different etiologies.

a) *Nosema*-infected colonies naturally recover during the summer
b) fumagillin loses its efficacy or
c) fumagillin becomes depleted from colony honey stores In humans, Fumagillin was used more than 40 years ago for the treatment of intestinal amebiasis, and it is effective when used topically. However, a recent study showed that Fumigillin caused serious toxic side effects (neutropenia and thrombocytopenia) in patients that were treated for microsporidiosis due to *Enterocytozoon bieneusi.*

Of further concern is the possibility that *Nosema*, multiplying in the millions in each bee gut, will eventually develop resistance to Fumagillin, as has been the experience with other antibiotics that are copiously applied. Thus, possible resistance of *Nosema* to Fumagillin makes many beekeepers around the world understandably concerned about it's widespread use for prevention of *Nosema* infection. Due to these and other concerns, Fumagillin's use for treating *Nosema* in honeybees has already been prohibited in Europe.

*Nosema* and Microsporidian Genetics

Several Microsporidian genomes, including the human *Encephalitozoon cuniculi* (*E. cunuculi*), have been published to date. The sequence analysis of *E. cuniculi* revealed a very small and compacted genome of 2.9-megabase, comprising of nearly 2000 genes. Due to its extreme reduction, *E. cuniculi* genome lacks most of the introns and intergenic spacers usually found in eukaryotic genomes. The majority of the genes are also shorter than their corresponding homologues. In addition, in-depth analysis of the predicted genes showed absence of genes of some biosynthetic and metabolic pathways, while other such pathways included a relatively limited number of genes. Recent studies using the sequencing information have revealed some details of microsporidian evolution and metabolism such as homologues of bacterial ADP/ATP transporter suspected important in *E. cunuculi* energy metabolism.

Being an obligate parasite, *E. cuniculi*, and microsporidia in general, relies on its host to provide it with the energetic and metabolic needs. The compensation pathways, and their function, are poorly understood.

For many years, microsporidia were thought be lacking the mitochondria, and accordingly proposed to have evolved before the appearance of the eukaryotic mitochondria. *Nosema* lack electron transport chain and Kreb's cycle, however, recently a highly reduced organelle, extremely reduced both in size and biochemical complexity, called the mitosome was identified, a probable relic from a primitive mitochondrion. To date, only 20 mitosomal proteins were identified, in contrast to the yeast mitochondrion, which contains about 1000 proteins.

Recently, a draft sequence of the *Nosema ceranae* genome was published, enabling further analysis of protein homologies and revealing a significant homology to, while distinct diversity from the *E. cunuculi* genome, and only few genes orthologous with that of *S. cerevisae.*

Intracellular symbiotic organisms use mitochondrial carrier family proteins (MCF) in order to acquire various substrates, including ATP, from the host cell, in order to provide the energy for the protein transport and other necessary mitosomal activities. However, as the microsporidian genomes have apparently lost all of the genes for the MCF proteins, it is not known how the parasite's mitosome acquires the necessary ATP for its function. Several bacterial intracellular parasites, such as *Rickettsia*, possess a nucleotide transporter which is used for ATP import from their eukaryotic host cell. Homologues of these genes were identified in the *E. cuniculi* genome, however, the use of such bacterial-like nucleotide transporters to acquire ATP from a eukaryotic cell is unknown in a eukaryotic parasite. There are no homologues of these proteins in either vertebrate or invertebrate species sequenced to date.

Gene Silencing in Invertebrates

The process of post-transcriptional gene silencing is most likely a cellular defense mechanism used to prevent the expression of foreign genes, thought to be shared across kingdoms. The presence of long dsRNAs in cells stimulates the activity of a ribonuclease III enzyme referred to as Dicer, which is involved in the processing of the dsRNA into short pieces known as short interfering RNAs (siRNAs). These are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementarity to the antisense strand of the siRNA duplex. In some organisms, an amplification stage may follow the initiation stage of gene silencing, involving an RNA dependent RNA Polymerase (RdRP), which may subsequently lead to degradation of RNAs outside the initial dsRNA region of homology. It has been shown in some species that RNAi mediated interference spreads from the initial site of dsRNA delivery, producing interference phenotypes throughout the injected animal. In some invertebrates, including honeybees, a systemic interference defective (SID) gene encoding a transmembrane protein important to the systemic RNAi pathway has been identified. Apparently, these SID1-like proteins channel dsRNAs between cells, enabling a mechanism of systemic spread of the silencing signal. However, an invertebrate RdRP homologue has not yet been described. Recently, gene silencing by feeding viral dsRNA has been demonstrated effective in combating IAPV infection in honeybees (PCT IL2008/001440).

Microsporidia have been classified as Fungi, which have shown an evolutionarily diverse repertoire of silencing proteins. Some of these are distinct from vertebrate silencing homologues. In *Trypanosoma brucei* a DICER-like homologue was identified. RISC homologues have also been described, and RNAi-related transcripts have been identified in simple, parasitic eukaryotes such as *Giardia* and Trichomonas. However, the function of such enzymes and their products is unclear. Further, although DICER and RISC enzymes have been detected in some species of *Trypanosomes*, other *Trypanosomes* have been identified as RNAi-negative, consistent with the observation that many eukaryotic parasites are genetically heterogeneous where RNAi pathways are concerned (Ullu et al, 2004).

RNAi gene silencing in intracellular eukaryotic parasites has been demonstrated either for host proteins suspected of critical roles in the parasites life cycle (as in *T. cruzi*), or in free-living forms, such as the extra-cellular forms of *Plasmodium* and *T. brucei* that can be cultured in-vitro. As opposed to the numerous studies with viral parasites, to date, no endogenous gene silencing in intracellular forms of eukaryotic parasites has been demonstrated. In addition to the requirement of traversing at least one parasite membrane of undefined permeability and composition, additional obstacles to effective RNAi methodology for intracellular forms of eukaryotic parasites include the heterogeneity of RNAi pathways in lower, parasitic eukaryotes, poor understanding of the function of such pathways, and the limited knowledge of parasite metabolism, and therefore difficulty in selecting effective targets for silencing the parasite genes.

There is thus a need and it would be highly desirable to have methods for effective, gene silencing in *Nosema*, in order to prevent and treat *Nosema* infection in honeybees.

SUMMARY OF THE INVENTION

According to an aspect of some embodiments of the present invention there is provided an isolated nucleic acid agent comprising a nucleic acid sequence downregulating expression of a gene product of a *Nosema* parasite.

According to another aspect of some embodiments of the present invention there is provided a nucleic acid construct comprising an isolated nucleic acid agent comprising a nucleic acid sequence downregulating expression of a gene product of a *Nosema* parasite.

According to yet another aspect of some embodiments of the present invention there is provided a bee-ingestible composition comprising an isolated nucleic acid agent comprising a nucleic acid sequence downregulating expression of a gene product of a *Nosema* parasite.

According to some embodiments of the invention the bee-ingestible composition is in solid form.

According to some embodiments of the invention the bee-ingestible composition is in liquid form.

According to some embodiments of the invention the bee-ingestible composition comprises protein.

According to some embodiments of the invention the protein is in the form of pollen and/or soy patties.

According to some embodiments of the invention the liquid is a sucrose solution or a corn syrup solution.

According to some embodiments of the invention the liquid further comprises a carbohydrate or sugar supplement.

According to still another aspect of some embodiments of the present invention there is provided a method for reducing the susceptibility of a bee to a *Nosema* infection comprising feeding the bee an effective amount of an isolated nucleic acid agent comprising a nucleic acid sequence downregulating expression of a gene product of a *Nosema* parasite, thereby reducing the susceptibility of the bee to the *Nosema* infection.

According to an aspect of some embodiments of the present invention there is provided a method for reducing the susceptibility of a bee to a *Nosema* infection comprising feeding the bee an effective amount of the nucleic acid agent comprising nucleic acid sequences downregulating the expression of at least one *Nosema* ATP/ADP transporter protein or homologue thereof and least one *Nosema* mitosomal protein, thereby reducing the susceptibility of said bee to the *Nosema* infection.

According to another aspect of some embodiments of the present invention there is provided a method of reducing the susceptibility of honeybees to *Nosema* infection, the method comprising feeding to the honeybee hive an effective amount of double stranded ribonucleic nucleic acid (dsRNA), said double stranded RNA comprising at least one sequence complementary to at least 21 nucleotides of a *Nosema*-specific mRNA and capable of inducing degradation of the *Nosema*-specific mRNA.

According to some embodiments of the invention the gene product is an mRNA encoding a *Nosema* polypeptide.

According to some embodiments of the invention the agent is selected from the group consisting of a dsRNA, an antisense RNA and a ribozyme.

According to some embodiments of the invention the dsRNA is selected from the group consisting of siRNA, shRNA and miRNA.

According to some embodiments of the invention the nucleic acid sequence is greater than 15 base pairs in length.

According to some embodiments of the invention the nucleic acid sequence is 19 to 25 base pairs in length.

According to some embodiments of the invention the nucleic acid sequence is greater than 30 base pairs in length.

According to some embodiments of the invention the *Nosema* parasite is *N. ceranae* or *N. apis.*

According to some embodiments of the invention the *Nosema* parasite is *N. ceranae* and the gene product is an mRNA encoding a *Nosema* mitosomal protein.

According to some embodiments of the invention the *Nosema* mitosomal protein is selected from the group consisting of TOM70, T1M22, TOM40, Imp2, mitochondrial Hsp70, ATM1-ABC transporter proteins, Frataxin, Ferredoxin, ERV1, ferredoxin, NADPH oxido-reductase [FNR], pyruvate dehydrogenase α subunit, pyruvate dehydrogenase β subunit, mitochondrial glycerol-3-phosphate dehydrogenase (mtG3PDH), manganese-containing superoxide dismutase (MnSOD), DNAJ (Hsp70 interacting), Iron Sulfur cluster ISU1, Cystein desulfurase Nsf1, NAR1 and RLI1.

According to some embodiments of the invention the nucleic acid sequence is complementary to a sequence as set forth in any of SEQ ID NOs: 55-252698.

According to some embodiments of the invention the *Nosema* parasite is *N. ceranae* and the gene product is an mRNA encoding a *Nosema* ATP/ADP transporter protein or homologue thereof.

According to some embodiments of the invention the ATP/ADP transporter protein or homologue thereof is selected from the group consisting of proteins encoded by SEQ ID NOs: 44, 45, 46 and 47.

According to some embodiments of the invention the isolated nucleic acid agent comprises at least two nucleic acid sequences downregulating expression of a gene product of a *Nosema* parasite. The at least two nucleic acid sequences can be contiguous or non-contiguous with respect to one another.

According to some embodiments of the invention nucleic acid sequences downregulate the expression of at least two *Nosema* mitosomal proteins.

According to some embodiments of the invention the nucleic acid sequences downregulate the expression of at least one *Nosema* ATP/ADP transporter protein or homologue thereof and least one *Nosema* mitosomal protein.

According to some embodiments of the invention the nucleic acid sequences comprise at least one nucleic acid sequence complementary to the sequence as set forth in SEQ ID NO: 59 and at least one nucleic acid sequence complementary to a sequence as set forth in SEQ ID NOs: 57 and 58.

According to some embodiments of the invention the nucleic acid sequences comprise a plurality of sequences having at least one nucleic acid sequence complementary to a sequence as set forth in each of SEQ ID NO: 59, 55, 56, 57 and 58.

According to some embodiments of the invention the bee is a honeybee, a forager, or a hive bee.

According to some embodiments of the invention the *Nosema* infection is a *Nosema ceranae* or a *Nosema apis* infection.

According to some embodiments of the invention the infection is a *Nosema ceranae* infection and feeding the effective amount of the nucleic acid agent reduces mortality from the infection.

According to some embodiments of the invention the nucleic acid agent comprises a nucleic acid sequence selected complementary to any of the sequences as set forth in the group consisting of SEQ ID NOs: 55-252698.

According to some embodiments of the invention the nucleic acid agent comprises a plurality of nucleic acid sequences complementary to any of the sequences as set forth in each of the group consisting of SEQ ID NOs: 57, 58 and 59.

According to some embodiments of the invention the feeding comprises providing a liquid bee-ingestible composition.

According to some embodiments of the invention the feeding comprises providing a solid bee-ingestible composition.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

Figure 1:
Figure 1:
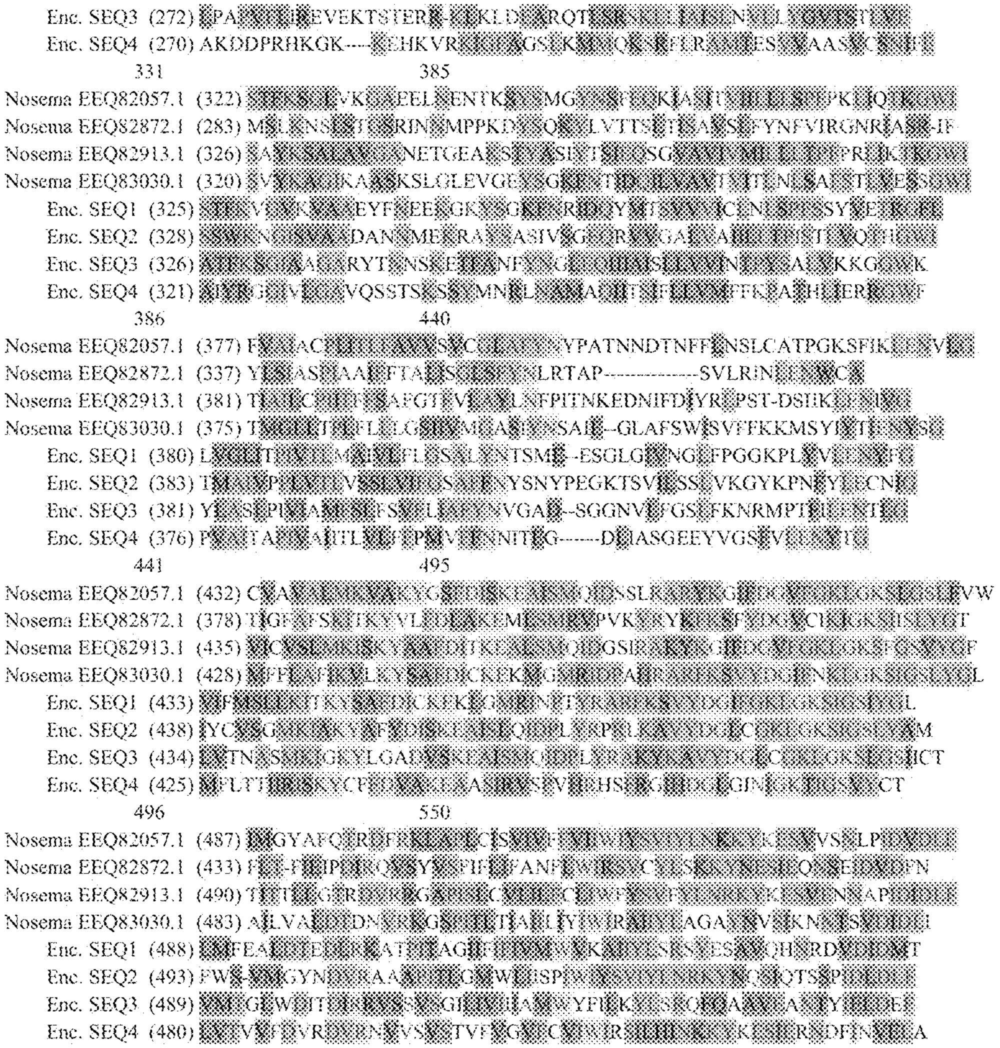
Figure 2:
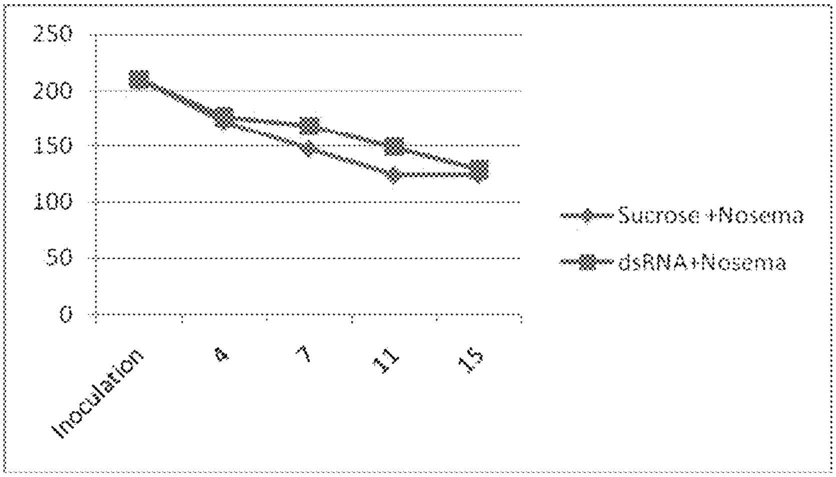
Figure 3:
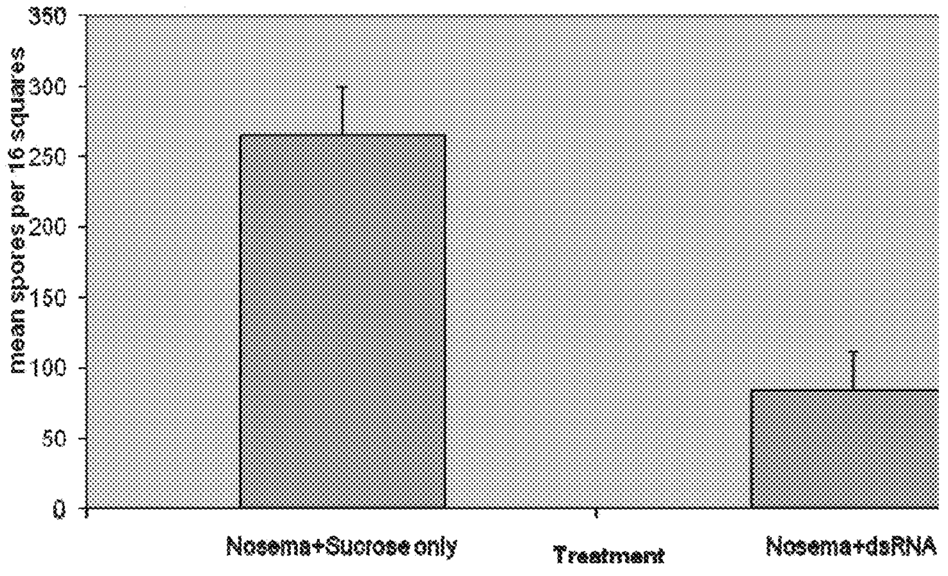
Figure 4:
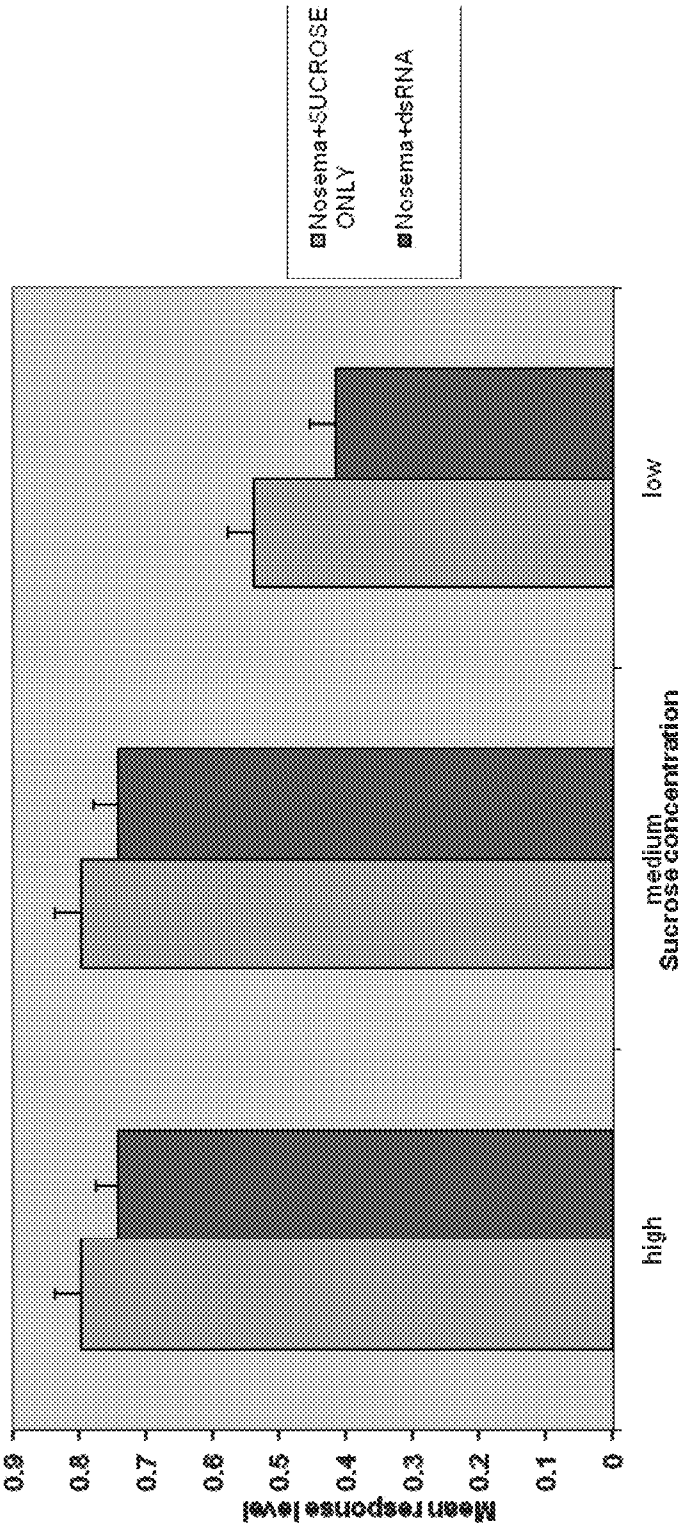
Figure 5:
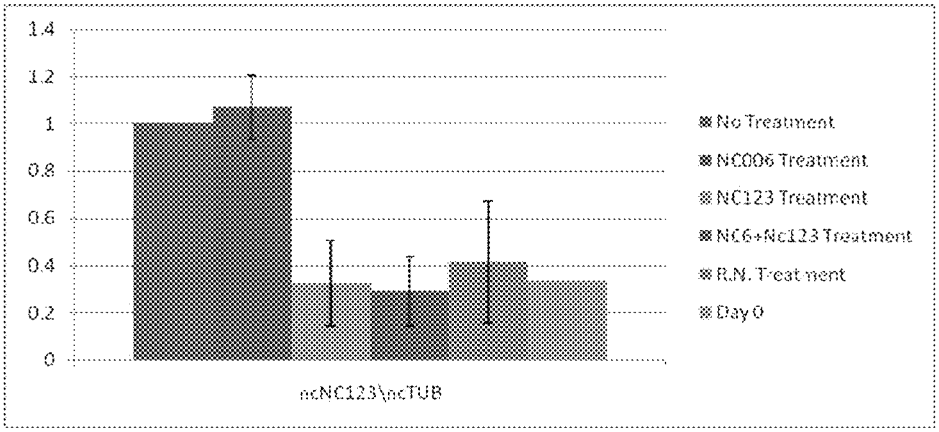
Figure 6:
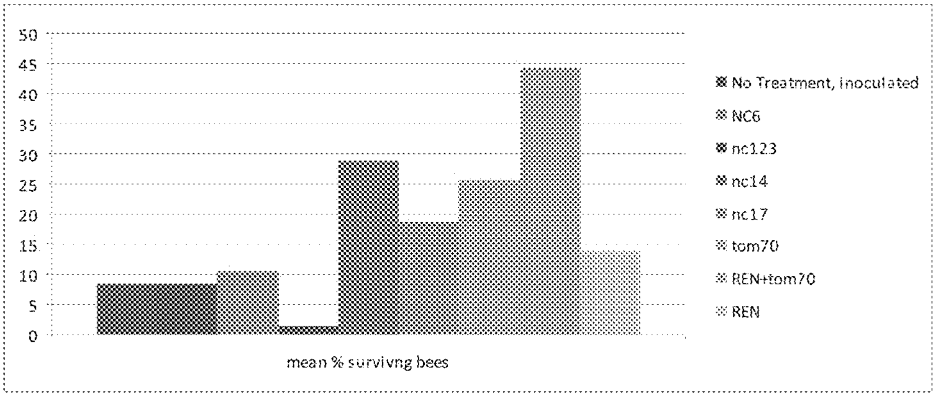
Figure 7:
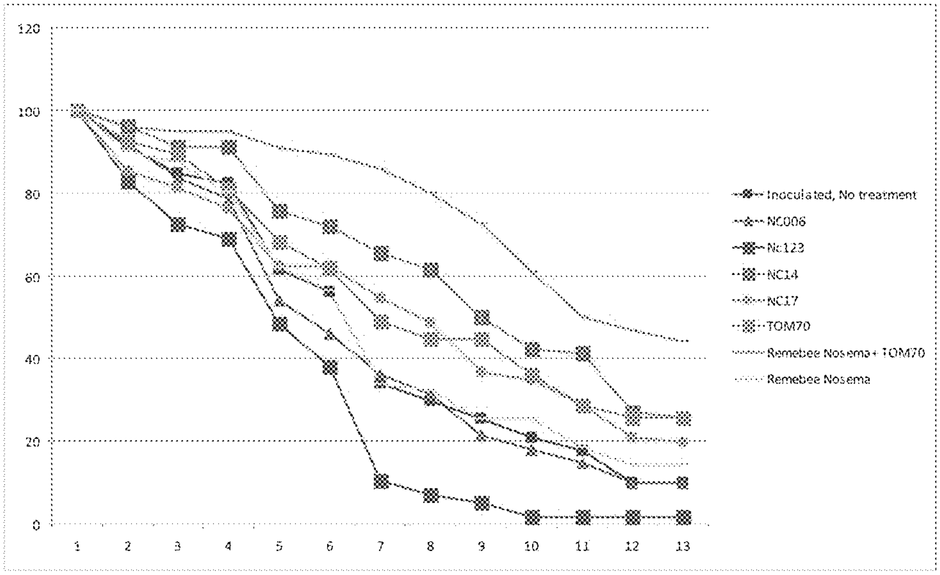
Figure 8:
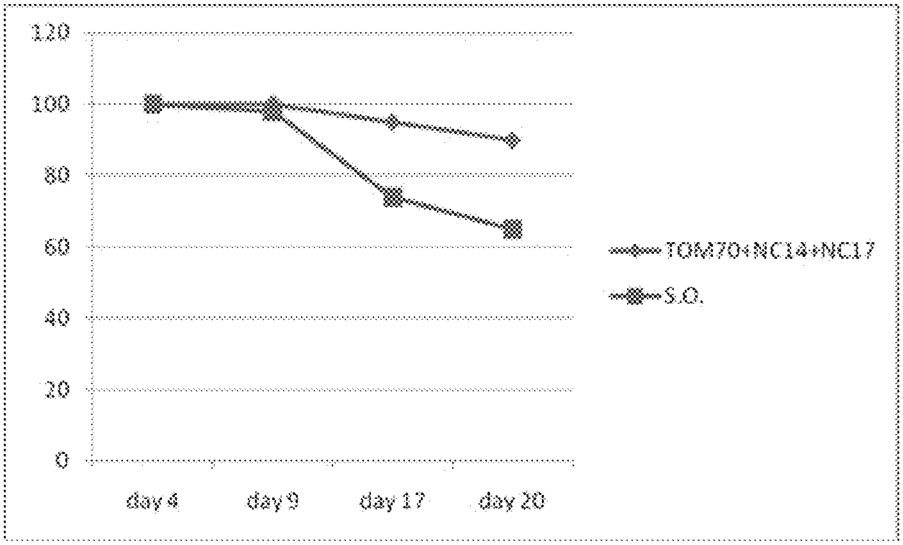
Figure 9:
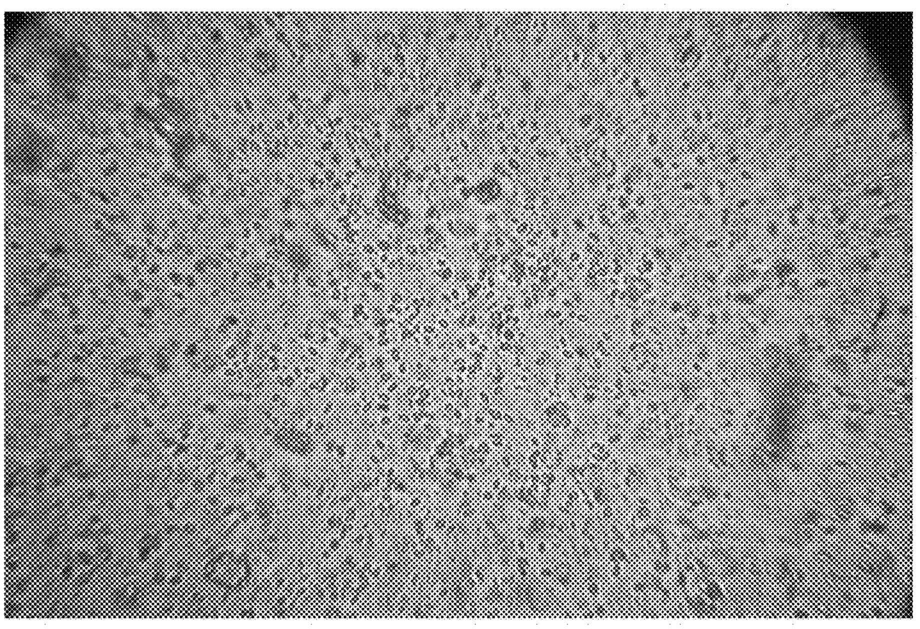
Figure 10:
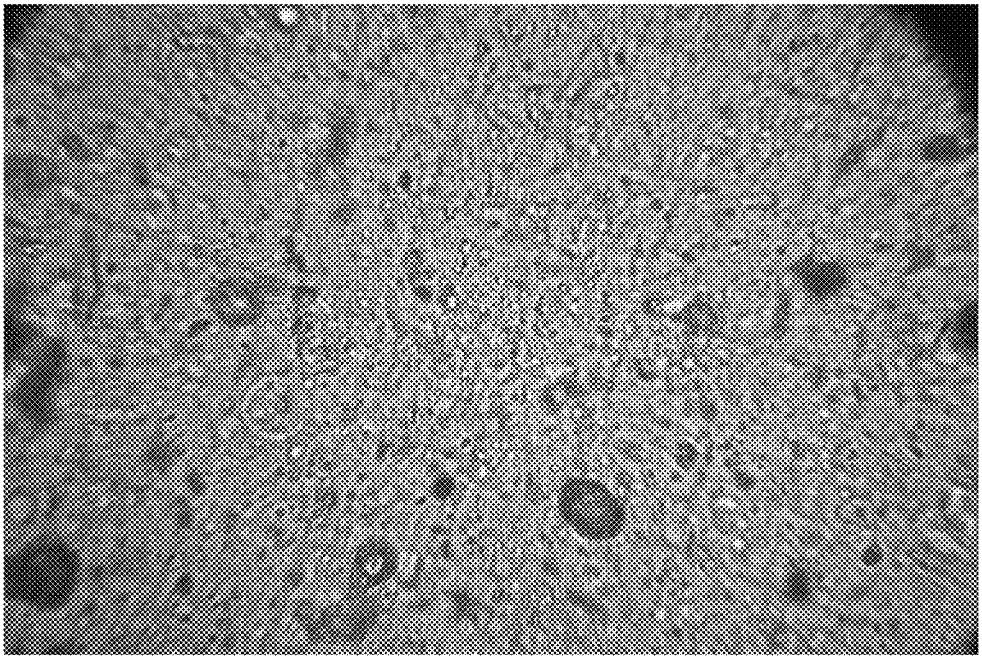
Figure 11:
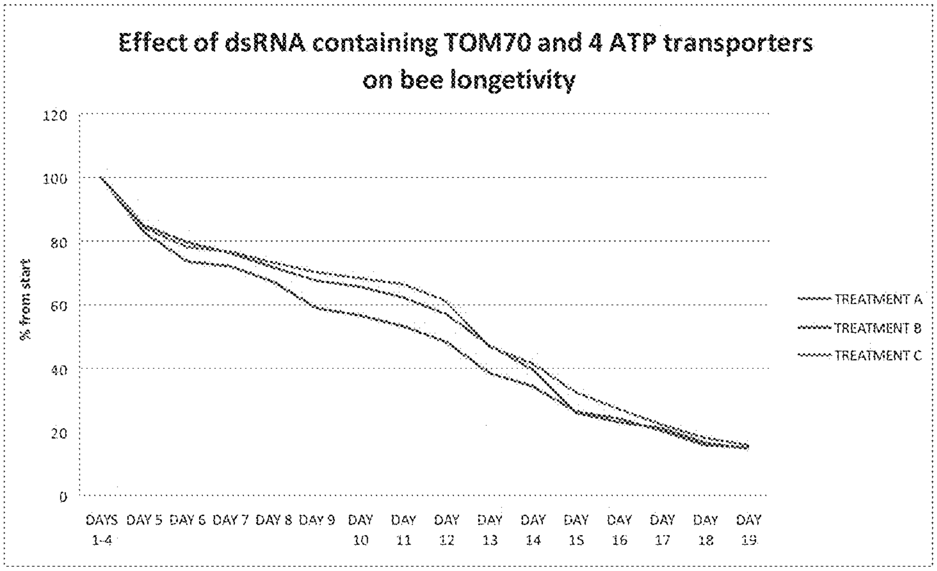

FIG. 1 is an alignment of *E. cuniculi* ATP transport protein sequences (Enc SEQ 1 is SEQ ID NO: 23; Enc SEQ 1 is SEQ ID NO: 24; Enc SEQ 1 is SEQ ID NO: 25; Enc SEQ 1 is SEQ ID NO: 26), and the homologues found in *N. ceranae*. EEQ82075.1 is SEQ ID NO: 27; EEQ83030.1 is SEQ ID NO: 44; EEQ82913.1 is SEQ ID NO: 46 and SEQ82872.1 is SEQ ID NO: 47;

FIG. 2 is a graph showing enhanced survival of bees fed dsRNA of *N. ceranae* ATP/ADP transport protein homologues. The Y-axis represents the number of surviving bees counted per minihive, at each time point and the X-axis represents the number of days from inoculation with *N. cerana*. N=6 minihives per treatment;

FIG. 3 is a histogram showing reduced *Nosema* spore levels in bees found dead following feeding of hives and boxes with dsRNA of *N. ceranae* ATP/ADP transport protein homologues. Dead bees succumbing to *Nosema* infection in box and minihive experiments were collected from day 7 to day 15 post infection, and spores prepared for counting in a haemacytometer as described herein. Uninfected bees (no *Nosema* spores detected) were excluded from the samples. Y-axis is mean spore count per 16 squares. N=75 samples. Note that feeding the dsRNA of *N. ceranae* ATP/ADP transport protein homologues resulted in greater than three-fold lower spore count in the dead, infected bees, compared with untreated controls;

FIG. 4 is a histogram showing reduced hunger in bees fed with dsRNA of *N. ceranae* ATP/ADP transport protein homologues. Hunger, expressed as the tendency of positive response in the Proboscis Extension Reflex (PER) assay, was consistently greater among untreated, infected control bees (*Nosema*+Sucrose only) than bees fed with dsRNA of *N. ceranae* ATP/ADP transport protein homologues (*Nosema*+dsRNA). N=1000 total responses. Note that the increased threshold for PER response among bees fed with dsRNA of *N. ceranae* ATP/ADP transport protein homologues is most clearly evident at low (<1%) sucrose concentrations, indicating reduced metabolic stress in the treated bees;

FIG. 5 is a histogram illustrating the specific silencing of *Nosema* gene expression by dsRNA of *N. ceranae* ATP/ADP transport protein homologues. Levels of gene expression of *Nosema* ATP/ADP transporter protein homologue NC123 in bees fed *Nosema* specific dsRNA was assayed by real-time PCR, normalized in relation to *Nosema* tubulin gene expression, and expressed in relation to NC123 expression in *Nosema*-infected bees fed sucrose only (no treatment), which was given a value of 1. Column titles from left to right: No treatment, NC006 Treatment (fed dsRNA of NC006 protein), NC123 Treatment (fed dsRNA of NC123 protein), NC6+Nc123 Treatment (fed combined dsRNA of NC006 and dsRNA of Nc123 protein), R.N. Treatment (fed combined dsRNA of NC006 protein, dsRNA of Nc123 protein, dsRNA of Nc014 protein and dsRNA of Nc017 protein) and Day 0 (uninfected). Note the significant reduction of transcript number, only among bees fed the dsRNA in which the NC123-specific homologous dsRNA was present;

FIG. 6 is a histogram illustrating enhanced survival in bees fed dsRNA of *N. ceranae* mitosomal and non-mitosomal proteins. Mean % of the bees in a minihive surviving at day 14 following *Nosema* infection is indicated for bees fed *Nosema* specific dsRNA of *N. ceranae* mitosomal and non-mitosomal energy-related protein homologues. Column titles, starting from second from the left: No treatment, infected, NC6 (fed dsRNA of *Nosema* NC006 protein), NC123 Treatment (fed dsRNA of *Nosema* NC123 protein), NC14 (fed dsRNA of *Nosema* Nc014 protein), NC17 (fed dsRNA of *Nosema* Nc017 protein), TOM70 (fed dsRNA of *Nosema* Nc014 protein), REN+TOM70 (fed combined dsRNA of *Nosema* NC006 protein, dsRNA of Nc123 protein, dsRNA of Nc014 protein, dsRNA of Nc017 protein and dsRNA of TOM70 protein) and REN (fed combined dsRNA of NC006 protein, dsRNA of Nc123 protein, dsRNA of Nc014 protein and dsRNA of Nc017 protein). Note the significant enhancement of survival with feeding of some, but not all of the *Nosema*-specific dsRNA (e.g. nc014, nc017 and TOM70), and the synergic effect of feeding combined nc006, nc123, nc014, nc017 and TOM70 dsRNA;

FIG. 7 is a graph showing the enhanced survival in bees fed dsRNA of *N. ceranae* mitosomal and non-mitosomal proteins, as percent surviving bees following infection, expressed over the entire duration of the experiment. Legend: No treatment, infected (■), NC6 (fed dsRNA of *Nosema* NC006 protein) (▲), NC123 Treatment (fed dsRNA of *Nosema* NC123 protein) (■), NC14 (fed dsRNA of *Nosema* Nc014 protein) (□x), NC17 (fed dsRNA of *Nosema* Nc017 protein) (●), TOM70 (fed dsRNA of *Nosema* Nc014 protein) (▒) REN+TOM70 (fed combined dsRNA of *Nosema* NC006 protein, dsRNA of Nc123 protein, dsRNA of Nc014 protein, dsRNA of Nc017 protein and dsRNA of TOM70 protein) (▼) and REN (fed combined dsRNA of NC006 protein, dsRNA of Nc123 protein, dsRNA of Nc014 protein and dsRNA of Nc017 protein) (—). Note the consistently superior survival rate among the bees fed combined nc006, nc123, nc014, nc017 and TOM70 dsRNA (▼);

FIG. 8 is a graph illustrating enhanced survival of bees fed dsRNA of a combination of *N. ceranae* mitosomal and non-mitosomal proteins, as percent surviving bees, following infection, expressed over the entire duration of the experiment. Significantly reduced mortality was observed in minihives of bees fed combined dsRNA of *Nosema ceranae* Nc014 protein, Nc017 protein and TOM70 protein (TOM70+NC14+NC17, ♦), compared to untreated bees (S.O., ■);

FIG. 9 is a photomicrograph illustrating the high *Nosema* spore count characteristic of surviving bees fed combined dsRNA of *Nosema ceranae* Nc014 protein, Nc017 protein and TOM70 protein, 21 days after infection;

FIG. 10 is a photomicrograph illustrating the absence of *Nosema* spores in the surviving, untreated control bees fed sucrose only, 21 days after infection;

FIG. 11 is a graph illustrating the enhanced survival of bees fed dsRNA of *N. ceranae* mitosomal and non-mitosomal proteins, as percent surviving bees following infection, expressed over the entire duration of the experiment. Legend: No treatment, un-infected (Treatment A), No treatment, infected (Treatment B) and feeding combined dsRNA of *Nosema* NC006 protein, dsRNA of Nc123 protein, dsRNA of Nc014 protein, dsRNA of Nc017 protein and dsRNA of TOM70 protein (Treatment C). Note the consistently superior survival rate among the bees fed combined nc006, nc123, nc014, nc017 and TOM70 dsRNA (Treatment C).

DESCRIPTION OF EMBODIMENTS OF THE INVENTION

The present invention, in some embodiments thereof, relates to methods and compositions for reducing the susceptibility of bees to *Nosema* infection and/or reducing the severity of *Nosema* infections by feeding *Nosema*-specific dsRNA.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While reducing the present invention to practice, the inventors have shown that ingestion by a bee of compositions containing one or more dsRNA molecules, wherein at least one segment of the dsRNA molecule corresponds to a substantially identical segment of *Nosema* mitosomal protein RNA and/or one or more non-mitosomal ATP/ADP transporter homologues, will result in reduced incidence and severity of a *Nosema* infection, and greatly enhanced survival of the bees and the colony overall. These results indicate that a polynucleotide molecule, either DNA or RNA, derived from a *Nosema* mitosomal protein and/or at least one additional non-mitosomal ATP/ADP transporter protein homologue sequence can be used to design a nucleic acid agent or nucleic acid construct according to the methods of the present invention to produce one or more RNA sequences that can form into a dsRNA molecule available for ingestion by bees when provided by feeding. While reducing to practice, it was shown that bee colonies exposed to *Nosema* mitosomal protein-specific dsRNA in their feed endured *Nosema* infection with greater survival (see FIGS. 2, 6-8 and 11) and lower incidence of fatally infected bees than untreated colonies (see FIGS. 3 and 8-10), and that *Nosema* mitosomal protein-specific dsRNA provided together with non-mitosomal ATP/ADP transporter protein homologue dsRNA was synergic in its protective effect.

Thus, according to one embodiment of the present invention there is provided a method for reducing the susceptibility of a bee to a *Nosema* infection comprising feeding the bee an effective amount of an isolated nucleic acid agent comprising a nucleic acid sequence downregulating expression of a *Nosema* gene product, or a nucleic acid construct comprising the nucleic acid sequence, thereby reducing the susceptibility of the bee to the *Nosema* infection.

As used herein, the term "bee" is defined as any of several winged, hairy-bodied, usually stinging insects of the superfamily Apoidea in the order Hymenoptera, including both solitary and social species and characterized by sucking and chewing mouthparts for gathering nectar and pollen. Exemplary bee species include, but are not limited to *Apis*, *Bombus*, *Trigona*, *Osmia* and the like. In one embodiment, bees include, but are not limited to bumblebees (*Bombus terrestris*) and honeybees (*Apis mellifera*).

As used herein, the term "colony" is defined as a population of dozens to typically several tens of thousand honeybees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honeybees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage.

As used herein, the term "tolerance" is defined as the ability of a bee or bee colony to resist and/or endure infestation by and/or proliferation of a *Nosema* pathogen, including, but not limited to, degree of infection, severity of symptoms, infectivity to other individuals (contagion), and the like. Tolerance can be assessed, for example, by monitoring bee longetivity/life-span, infectivity, presence of symptoms, such as, but not limited to, hunger, vitality, flight range, etc, presence of pathogenic organisms, or time course of a disease in a population following a challenge with the *Nosema* pathogen.

As used herein, the term "susceptibility" is defined as the ability of a bee or bee colony to become infested or infected by and/or support proliferation of a *Nosema* pathogen, including, but not limited to, degree of infection, severity of symptoms, infectivity to other individuals (contagion), and the like. Susceptibility can be assessed, for example, by monitoring infectivity, presence of symptoms, such as, but not limited to, hunger, vitality, flight range, etc, presence of pathogenic organisms, mortality or time course of a disease in an individual bee or bee population following a challenge with the *Nosema* pathogen.

As used herein, the term "*Nosema*" is defined as any organism of a genus (the type of the family Nosematidae) of microsporidian protozoans that includes various parasites, particularly those causing disease in bees or bee colonies. *Nosema* infecting bee include but are not limited to *N. ceranae* and *N. apis*. Infection of bees or bee colonies with a *Nosema* parasite is commonly known as Nosemosis. It will be appreciated that the gene silencing mechanisms described herein can be effective for combating microsporidean species infecting hosts other than bees, with examples including but not limited to, the silk moth, and humans. However, due to the heterogeneity of RNAi and metabolic pathways in microsporidia, and in view of the critical role of the individual parasite's endogenous RNAi pathways for effective gene silencing, identification of effective candidate target genes may be required in each case.

As used herein, the term "mitosome" is defined as a double membrane-bound mitochondria-like organelle of Microsporidia highly reduced from the perspective of both physical size and biochemical complexity. Mitosomal proteins include, but are not limited to protein and metabolite import proteins (TOM70, T1M22, TOM40, Imp2, mitochondrial Hsp70, and ATM1-ABC transporter proteins), proteins involved in ISC assembly and export (frataxin, ferredoxin, ISCU, ISCS, ERV1, and ferredoxin NADPH oxido-reductase [FNR]), pyruvate dehydrogenase subunits, PDH$\alpha$ and -$\beta$, mitochondrial glycerol-3-phosphate dehydrogenase (mtG3PDH) and manganese-containing superoxide dismutase (MnSOD).

As used herein, the term "ATP/ADP transporter protein" refers to a protein which function is transfer of ATP and/or ADP through membranes. Microsporidian ATP/ADP transporter proteins homologous to ATP/ADP transporter proteins from other species have been identified in *E. cuniculi* and *N. ceranae*(see above, and FIG. 1). As used herein, "putative" ATP/ADP transporter proteins, "ATP/ADP transporter protein orthologues" or "ATP/ADP transporter protein homologues" refer to proteins, or putative encoded polypeptides from polynucleotide sequences, having significant amino acid identity or similarity to known ATP/ADP transporter proteins of other species, and/or possessing consensus sequences common to known ATP/ADP transporter proteins. Examples of *Nosema* ATP/ADP transporter proteins, or ATP/ADP transporter protein homologues, are nc123 (SEQ ID NO:19), nc006 (SEQ ID NO:22), nc014 (SEQ ID NO:21) and nc017 (SEQ ID NO:20).

As used herein, the terms "bee disease" or "bee colony disease" are defined as undesirable changes in the behavior, physiology, morphology, reproductive fitness, economic value, viability, honey production, pollination capability, resistance to infection and/or infestation of a bee, a population of bees and/or a bee colony, directly or indirectly resulting from contact with a *Nosema* parasite or a *Nosema*-infected bee or other organism.

A draft of the genome of *N. ceranae* has been provided in Cornman et al. 2009 Plos Pathogen.

While reducing the present invention to practice, the inventors have shown that providing *Nosema* mitosomal-specific dsRNA, alone or in combination with dsRNA specific to additional non-mitosomal *Nosema* ATP/ADP transporter protein homologues in the feed of bees exposed to *Nosema* dramatically reduced the incidence and levels of *Nosema* sequences detected in the bees (see FIG. 5). Thus, in some embodiments of the present invention, the methods and compositions are useful for downregulating expression of a *Nosema* mitosomal or non-mitosomal polypeptides in a bee.

As used herein, the term "downregulating expression" is defined as causing, directly or indirectly, reduction in the transcription of a desired gene, reduction in the amount, stability or translatability of transcription products (e.g. RNA) of said gene, reduction in translation of the polypeptide(s) encoded by the desired gene and/or reduction in the amount, stability, or alteration of biochemical function of the polypeptides encoded by the desired gene, so as to reduce the amount or function of the gene products. As used herein, "downregulating expression" also relates to reduction in amount, stability or translatability of *Nosema* mitosomal or non-mitosomal RNA molecules in cells of a bee. Downregulating expression of a *Nosema* gene RNA can be monitored, for example, by direct detection of gene transcripts (for example, by PCR), by detection of polypeptide(s) encoded by the gene or bee *Nosema* RNA (for example, by Western blot or immunoprecipitation), by detection of biological activity of polypeptides encode by the gene (for example, catalytic activity, ligand binding, and the like), or by monitoring changes in a cell or organism resulting from reduction in expression of a desired *Nosema* gene or *Nosema* RNA (for example, reduced proliferation of a *Nosema* parasite, reduced virulence of a *Nosema* parasite, etc). It will be appreciated that changes in the course, severity, duration, etc. of a *Nosema* infection can be monitored in some instances via observation of the host, and/or host colony as well as direct observation of the parasite. This direct observation can be useful in instances where *nosema* virulence in relation to honeybee genotype is high. As used herein, the downregulation can be transient, for example, for the duration of the presence of a downregulating agent, or permanent, resulting in reduction of *Nosema* gene expression or RNA for the lifetime of the organism and/or its future generations.

Downregulation of *Nosema* mitosomal or non-mitosomal polypetides can be effected on the genomic and/or the transcript level using a variety of molecules which interfere with transcription and/or translation (e.g., RNA silencing agents, Ribozyme, DNAzyme and antisense). Treatment and prevention of viral infections with dsRNA has been disclosed by WO/2003/004649 to Tenllado et al and PCT patent application IL2008/001440 to Paldi et al. Use of dsRNA in insects is disclosed in US Patent Application 2007 0250947, US Patent Application 2006 0272049, PCT Applications WO 2007/080127 and WO 2007/080126, US patent application 20030150017, PCT patent application WO 02/14472, US Patent Application 20030154508, PCT patent application WO 2004/005485, PCT application WO 99/32619 and U.S. Pat. No. 6,326,193.

Following is a list of agents capable of downregulating expression level and/or activity of *Nosema* mitosomal polypeptides.

Downregulation of *Nosema* mitosomal and non-mitosomal polypeptides can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene or *Nosema* mitosomal RNA sequence. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference commonly refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to downregulate protein expression from mRNA.

According to one embodiment, the dsRNA is greater than 30 bp. The use of long dsRNAs can provide numerous advantages in that the cell can select the optimal silencing sequence alleviating the need to test numerous siRNAs; long dsRNAs will allow for silencing libraries to have less complexity than would be necessary for siRNAs.

In one embodiment of the present invention, the dsRNA is greater than 30 basepairs, and is selected from the group complementary to a sequence as set forth in SEQ ID NOs: 55-59. In another embodiment of the present invention, the dsRNA is greater than 30 base pairs and comprises at least two sequences complementary to a sequence selected from group as set forth in SEQ ID NOs: 55-59. In yet another embodiment, the dsRNA comprises the sequence complementary to the sequence as set forth in SEQ ID NO: 59 and to a sequence as set forth in at least one of SEQ ID NOs: 57 and 58. In one embodiment of the present invention, the dsRNA comprises at least two sequences downregulating expression of a target *Nosema* gene, wherein the at least two sequences can be contiguous, or non-contiguous with respect to one another.

Another method of downregulating *Nosema* mitosomal and/or non-mitosomal proteins is by introduction of small inhibitory RNAs (siRNAs).

The term "siRNA" refers to small inhibitory RNA duplexes (generally between 18-30 basepairs, between 19 and 25 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

According to one embodiment of the present invention, the nucleic acid agent is capable of causing cleavage and/or degradation of a *Nosema* mitosomal and/or non-mitosomal target polynucleotide sequence. As used herein, the phrases "target" or "target polynucleotide sequence" refer to any sequence present in a *Nosema* cell, whether naturally occurring sequence or a heterologous sequence present due to an intracellular or extracellular pathogenic infection or a disease (e.g. Nosemosis), which *Nosema* mitosomal or non-mitosomal polynucleotide sequence has a function that is desired to be reduced or inhibited. The *Nosema* target sequence may be a coding sequence, that is, it is translated to express a protein or a functional fragment thereof. Alternatively, the target sequence may be non-coding, but may have a regulatory function, or it may be without any known function. As described herein, one target polynucleotide sequence is a *Nosema* mitosomal polynucleotide sequence necessary for proteins involved in energy transfer, such as that of *Nosema* mitosomal ATP transporter homologues or metabolite import proteins, combinations of the same, alone or in combination with polynucleotide sequences targeting *Nosema* non-mitosomal proteins such as non-mitosomal ATP/ADP transporter homologues. The term "gene" is intended to include any target sequence intended to be "silenced", whether or not transcribed and/or translated, including regulatory sequences, such as promoters, enhancers and other non-coding sequences.

In one embodiment of the present invention, synthesis of RNA silencing agents suitable for use with the present invention can be effected as follows. First, the *Nosema* polypeptide mRNA or other target sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl Chem Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (see Ambion technical library 91/912 at the Ambion website).

Second, potential target sites are compared to an appropriate genomic database (e.g., human, mouse, rat, insect, etc.) using any sequence alignment software, such as the BLAST software available from the NCBI server of the NIH. Putative target sites which exhibit significant homology to other coding sequences are filtered out. For example, host (e.g. bee) target sites can be filtered out in this manner.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene or sequence for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to host gene sequences, or non-relevant *Nosema* target sequences.

For example, a suitable *Nosema* siRNA can be an *Nosema* specific siRNA corresponding to *Nosema ceranae* sequences SEQ ID NOs: 27, 47 and 46. Additional suitable *Nosema* siRNAs can be designed according to sequences from any *Nosema*, for example, including, but not limited to *Nosema apis, Nosema bombi, Nosema bombycis, Nosema antheraeae, E. cuniculi* and the like. According to one specific embodiment, the *Nosema* mitosomal target sequences are ADP/ATP transporter homologue 123 and/or the mitosomal metabolite transport protein TOM 70, and any or all of the non-mitosomal ADP/ATP transporter homologues, Nc 006, Nc 014 and Nc 017. Primer sequences for producing nucleic acid agents for silencing these genes are detailed in Table 1.

TABLE 1

*Nosema*-specific dsRNA sequences for silencing ATP/ADP transporter homologues and TOM70 and the primer sequences used to make them

| Primer name ADP/ATP TRANSPORTER PROTEIN HOMOLOGUE | Sequence (SEQ ID NO) |
|---|---|
| NA7001 T7 Nc006 F | **CTAATACGACTCACTATAGGGAGA**<br>CAGCTAACGAGCCCGTTTC<br>(SEQ ID NO: 1) |
| NA7002 T7 Nc006 R | **CTAATACGACTCACTATAGGGAGA**C<br>CATAGTAATCCATCCACTAC<br>(SEQ ID NO: 2) |
| NA7003 T7 Nc123 F | **CTAATACGACTCACTATAGGGAGA**<br>CTGGTCTTTAACGAATGGAC<br>(SEQ ID NO: 3) |
| NA7004 T7 Nc123 R | **CTAATACGACTCACTATAGGGAGA**<br>GTGGGCACGCTATGGCAAC<br>(SEQ ID NO: 4) |
| NA7005 T7 Nc014 F | **CTAATACGACTCACTATAGGGAGA**<br>CTCCTGGACAGTCCGCTAG<br>(SEQ ID NO: 5) |
| NA7006 T7 Nc014 R | **CTAATACGACTCACTATAGGGAGA**GA<br>ATCAGTTGACGGTAAACGG<br>(SEQ ID NO: 6) |
| NA7007 T7 Nc017 F | **CTAATACGACTCACTATAGGGAGA**<br>GCTTGATGGGCTTATCTCC<br>(SEQ ID NO: 7) |
| NA7008 T7 Nc017 R | **CTAATACGACTCACTATAGGGAGA**<br>GCAATGCGATTTCCACGG<br>(SEQ ID NO: 8) |
| TOM-70 PROTEIN | |
| NT7009 T7 TOM70 F | **CTAATACGACTCACTATAGGGAGA**CT<br>GAATGTTACAAGCAGATGGG<br>(SEQ ID NO: 9) |
| NT7015 TOM70 R | **CTAATACGACTCACTATAGGGAGA**ACC<br>AGGAGTATCTGGATGAC<br>(SEQ ID NO: 10) |

*Note:
The *Nosema* specific sequences are in plain font.

Additional suitable *Nosema* siRNAs can be designed according to sequences from any *Nosema* sequence, for example, the sequences detailed herein, including, but not limited to TOM70 (for example, SEQ ID NOs:60-11687), TIM22, TOM40 (for example, SEQ ID NOs: 11688-19103), Imp2, mitochondrial Hsp70 (for example, SEQ ID NOs: 19104-34511), ATM1-ABC transporter proteins (for example, SEQ ID NOs: 34512-80411), Frataxin, Ferredoxin, ERV1 (for example, SEQ ID NOs: 80412-84803), ferredoxin, NADPH oxido-reductase [FNR] (for example, SEQ ID NOs:84804-94911, 94912-108140), pyruvate dehydrogenase α subunit (for example, SEQ ID NOs: 108141-116852), pyruvate dehydrogenase β subunit (for example, SEQ ID NOs: 116853-125294), mitochondrial glycerol-3-phosphate dehydrogenase (mtG3PDH) (for example, SEQ ID NOs: 125295-140999), manganese-containing superoxide dismutase (MnSOD) (for example, SEQ ID NOs: 141000-146687), DNAJ (Hsp70 interacting) (for example, SEQ ID NOs: 146688-157505), Iron Sulfur cluster ISU1, Cystein desulfurase Nsf1 (for example, SEQ ID NOs: 157506-169079), NAR1 (for example, SEQ ID NOs: 169080-178790), RLI1 (for example, SEQ ID NOs:178791-195062), NC006 (for example, SEQ ID NOs: 195063-209633, NC123 (for example, SEQ ID NOs: 209634-224609), NC014 (for example, SEQ ID NOs: 224610-239747) and NC017 (for example, SEQ ID NOs:239748-252698) (see Table 2, below).

TABLE 2

| *Nosema* Proteins suitable for targeting with dsRNA | | | | |
|---|---|---|---|---|
| | Encephalitozoon GenBank (protein) | *Nosema* GenBank (protein) | *Nosema* GenBank (DNA)/ coordinates | SEQ ID NO: |
| TOM70 | | EEQ82075.1 | ACOL01000120/8001-9314 | SEQ ID NO: 27 |
| TIM22 | CAD25556.1 | — | | |
| TOM40 | CAD25408.1 | EEQ82411.1 | ACOL01000061/14217-15062 | SEQ ID NO: 28 |
| Imp2 | | | | |
| mitochondrial Hsp70 | NP_586360 | EEQ81757 | ACOL01000228.1/4051-5784 | SEQ ID NO: 29 |
| ATM1-ABC transporter proteins | CAD26030 | EEQ82581.1 | ACOL01000042/1310-3019 | SEQ ID NO: 30 |
| | | EEQ82586.1 | ACOL01000042/8786-10507 | SEQ ID NO: 31 |
| | | EEQ82587.1 | ACOL01000042/10905-12638 | SEQ ID NO: 32 |
| Frataxin | XP_965969 | — | | |
| Ferredoxin | NP_585988.1 | — | | |
| ERV1 | CAD25469 | EEQ82883 | ACOL01000016/5063-5572 | SEQ ID NO: 33 |
| ferredoxin | CAD27143 | EEQ81930 | ACOL01000159/6191-7324 | SEQ ID NO: 34 |
| NADPH oxido-reductase [FNR] | | EEQ83026 | ACOL01000006/2688-4190 | SEQ ID NO: 35 |
| pyruvate dehydrogenase subunits, PDHα and -β | CAD27078 | EEQ82465 | ACOL01000055/12839-13828 | SEQ ID NO: 36 |
| | CAD25304 | EEQ81634 | ACOL01000316/888-1847 | SEQ ID NO: 37 |
| mitochondrial glycerol-3-phosphate dehydrogenase (mtG3PDH) | CAD25806 | EEQ82606 | ACOL01000039/538-2304 | SEQ ID NO: 38 |
| manganese-containing superoxide dismutase (MnSOD) | CAD26018 | EEQ82623 | ACOL01000038/17225-17878 | SEQ ID NO: 39 |
| DNAJ (Hsp70 interacting) | Q8SRK0 | EEQ82425 | ACOL01000059/6412-7635 | SEQ ID NO: 40 |
| Iron Sulfur cluster ISU1 | Q8SSM2 | — | | |
| Cystein desulfurase Nsf1 | Q8SQS2 | EEQ82825 | ACOL01000020/5924-7231 | SEQ ID NO: 41 |
| Critical Fe/S cytosolic proteins | | | | |
| NAR1 | NP_597440.1 | EEQ82578 | ACOL01000043/12613-13713 | SEQ ID NO: 42 |
| RLI1 | | EEQ83099 | ACOL01000003/27828-29657 | SEQ ID NO: 43 |
| ATP/ADP Transporter homologues | | | | |
| Nc006 | | EEQ83030.1 | ACOL01000006/9068-10708 | SEQ ID NO: 44 |
| Nc123 | | EEQ82057.1 | ACOL01000123/4795-6480 | SEQ ID NO: 45 |
| Nc014 | | EEQ82913.1 | ACOL01000014/4714-6417 | SEQ ID NO: 46 |
| Nc017 | | EEQ82872.1 | ACOL01000017/9811-11271 | SEQ ID NO: 47 |

It will be appreciated that the dsRNA sequences target RNA transcripts complementary to DNA sequences of the targeted gene which are expressed in the parasite (transcribed into RNA), and that the actual complementation taking place in the RNAi pathways occurs following reduction of the dsRNA to smaller fragments by the RNAi enzymes.

Multiple *Nosema* sequences can be designed to include sequences suitable for producing siRNAs effective against more than one *Nosema* species. Such multiple *Nosema* dsRNA can be of the long or short variety, and may also be combined with sequences corresponding to diverse classes of pathogens (e.g. viral and/or bacterial and/or fungal sequences, etc). Further, multiple sequences can be designed to include two or more dsRNA sequences of the same *Nosema* parasite.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIs1, TAT (48-60), pVEC, MTS, and MAP.

Another agent capable of downregulating a *Nosema* polypeptide is a DNAzyme molecule capable of specifically cleaving an mRNA transcript or DNA sequence of the *Nosema* polypeptide. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the “10-23” model) for the DNAzyme has been proposed. “10-23” DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

Downregulation of *Nosema* polypeptides or cleavage of *Nosema* RNA can also be effected by using an antisense polynucleotide capable of specifically hybridizing with an mRNA transcript encoding the *Nosema* polypeptide or a *Nosema* RNA target sequence.

Design of antisense molecules which can be used to efficiently downregulate a *Nosema* polypeptide must be effected while considering two aspects important to the antisense approach. The first aspect is delivery of the oligonucleotide into the cytoplasm of the appropriate cells, while the second aspect is design of an oligonucleotide which specifically binds the designated mRNA or RNA target sequence within cells in a way which inhibits translation thereof.

A number of delivery strategies which can be used to efficiently deliver oligonucleotides into a wide variety of cell types have been disclosed [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)]. Several approaches for designing and predicting efficiency of specific oligonucleotides using an in vitro system were also published (Matveeva et al., Nature Biotechnology 16: 1374-1375 (1998)].

For example, a suitable antisense oligonucleotide targeted against the *Nosema* mRNA would be of the sequences complementary to sequences as set forth in SEQ ID NOs: 27, 46 and 47.

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a *Nosema* polypeptide is a ribozyme molecule capable of specifically cleaving an mRNA transcript encoding a *Nosema* polypeptide. Ribozymes are being increasingly used for the sequence-specific inhibition of gene expression by the cleavage of mRNAs encoding proteins of interest [Welch et al., Curr Opin Biotechnol. 9:486-96 (1998)]. Ribozymes have been identified in insects (Webb et al, Science 2009; 326: 953), and used effectively for gene silencing in insects (Lee et al, FASEB J 2001; 15:2390-400).

An additional method of regulating the expression of a *Nosema* polypeptide gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721, 138 to Lawn.

The RNA, dsRNA, siRNA, or miRNA of the present invention may be produced chemically or enzymatically through manual or automated reactions or in vivo in an organism. RNA may also be produced by partial or total organic synthesis. Any modified ribonucleotide can be introduced by in vitro enzymatic or organic synthesis. The RNA may be synthesized by a cellular RNA polymerase or a bacteriophage RNA polymerase (e.g., T3, T7, SP6). If synthesized chemically or by in vitro enzymatic synthesis, the RNA may be purified prior to feeding or formulated in an acceptable carrier and provided as a liquid, solid or semi-solid to the bees. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

It will be appreciated that mechanisms other than dsRNA for targeting the *Nosema* ATP/ADP transporter homologues, or other mitosomal and non-mitosomal proteins can effectively block gene expression in the parasite, and therefore potentially reduce *Nosema* levels, severity of symptoms and contagiousness in the host bees. Any molecules capable of traversing the membrane of bee mucosal epithelial cells and able to disrupt *Nosema* mitosomal (such as a mitosomal ATP/ADP homologue or TOM) or non-mitosomal (such as a non-mitosomal ATP/ADP homologue) expression or activity, could potentially enter the *Nosema* parasite in the intracellular stage, and reduce infection levels and severity of symptoms in infected host bees. Examples of such drugs are small molecules, peptides, enzymes that interact with the ATP-ADP transporters such as kinase or phosphatase enzymes.

For transcription from a transgene in vivo or from an expression cassette, a regulatory region (e.g., promoter, enhancer, silencer, leader, intron and polyadenylation) may be used to modulate the transcription of the RNA strand (or strands). Therefore, in one embodiment, there is provided a nucleic acid construct comprising the nucleic acid agent. The nucleic acid construct can have polynucleotide sequences constructed to facilitate transcription of the RNA molecules of the present invention are operably linked to one or more promoter sequences functional in a host cell. The polynucleotide sequences may be placed under the control of an endogenous promoter normally present in the host genome. The polynucleotide sequences of the present invention, under the control of an operably linked promoter sequence, may further be flanked by additional sequences that advantageously affect its transcription and/or the stability of a resulting transcript. Such sequences are generally located upstream of the promoter and/or downstream of the 3' end of the expression construct. The term "operably linked", as used in reference to a regulatory sequence and a structural nucleotide sequence, means that the regulatory sequence causes regulated expression of the linked structural nucleotide sequence. "Regulatory sequences" or "control elements" refer to nucleotide sequences located upstream, within, or downstream of a structural nucleotide sequence, and which influence the timing and level or amount of transcription, RNA processing or stability, or translation of the associated structural nucleotide sequence. Regulatory sequences may include promoters, translation leader sequences, introns, enhancers, stem-loop structures, repressor binding sequences, termination sequences, pausing sequences, polyadenylation recognition sequences, and the like.

The nucleic acid agent can be delivered to the bees in a great variety of ways. As detailed herein, bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g. brewer's yeast, torula yeast) and yeast products products-fed singly or in combination and soybean flour fed as a dry mix or moist cake inside the hive or as a dry mix in open feeders outside the hive. Also useful is sugar, or a sugar syrup. The addition of 10 to 12 percent pollen to a supplement fed to bees improves palatability. The addition of 25 to 30 percent pollen improves the quality and quantity of essential nutrients that are required by bees for vital activity.

Cane or beet sugar, isomerized corn syrup, and type-50 sugar syrup are satisfactory substitutes for honey in the natural diet of honey bees. The last two can be supplied only as a liquid to bees.

Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover. A supply of water must be available to bees at all times. In one embodiment, pan or trays in which floating supports-such as wood chips, cork, or plastic sponge—are present are envisaged. Detailed descriptions of supplemental feeds for bees can be found in, for example, USDA publication by Standifer, et al 1977, entitled "Supplemental Feeding of Honey Bee Colonies" (USDA, Agriculture Information Bulletin No. 413).

It will be appreciated that the dosing and treatment regimen of *Nosema*-specific nucleic acid agent can be optimized by the individual user according to host sub-species, weather conditions, stage in the life cycle of the host and/or parasite, host environmental conditions, etc. For example, the nucleic acid agent can be provided to the bees constantly, throughout the hives' lifetime, or according to a predetermined schedule of feeding.

All the bees in a hive are potentially susceptible to the *Nosema* infections detailed herein. Thus, according to some embodiments, the bees can be forager bees, hive bees and the like.

Also provided is a method for reducing the susceptibility of a bee to a disease caused by *Nosema*, the method effected by feeding the bee on an effective amount of a nucleic acid or nucleic acid construct comprising a nucleic acid agent downregulating expression of a *Nosema* mitosomal and/or non-mitosomal polypeptide and/or causing cleavage and/or degradation of a *Nosema* mitosomal or non-mitosomal RNA. Methods for reducing the susceptibility of a bee colony or bee-hive to *Nosema* infection or epidemic by feeding oligonucleotides and/or polynucleotides are envisaged. Thus, in some embodiments, the present invention can be used to benefit any numbers of bees, from a few in the hive, to the entire bee population within a hive and its surrounding area. It will be appreciated, that in addition to feeding of oligonucleotides and/or polynucleotides for reduction of the *Nosema* infection and infestation, enforcement of proper sanitation (for example, refraining from reuse of infested hives) can augment the effectiveness of treatment and prevention of infections.

It is expected that during the life of a patent maturing from this application many relevant methods for downregulating *Nosema* proteins will be developed and the scope of the term "downregulating *Nosema* protein" or "downregulating *Nosema* polypeptide" is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Plastic Box Protocol

Experimental Regimen

Bees were introduced into boxes (30-35 bees to each box) at study day 0, and placed in a room kept at a constant temperature of 25° C., 70% relative humidity and 12 hour light/dark cycle.

Nurse bees were collected from the entrance of a honeybee colony that was previously checked and no *N. ceranae* detected in the older forager bees. The bees were placed for several minutes in the cold to reduce activity. Subsequently, 30-35 bees were transferred into each box. The bees were observed during the first 2 days to determine stability in the boxes (i.e. no visible changes in the population). At study day 3 daily feeding of the treatment groups was initiated. The indicated amounts of all treatment components were added to the 66% sugar solution. All boxes were then monitored for bees' survival for up to an additional 21 days.

The boxes were then allocated randomly and equally to each treatment group.

Bees in the boxes were fed a sucrose syrup via a capillary tube sealed at its top end, thus avoiding drippage and enabling supply of feed upon demand. One feeding capillary tube was placed in each box.

Acclimation and Inclusion Criteria

The feeding capillaries were filled with 1.5 milliliters of 66% sucrose solution (w/v) and placed into the boxes (one in each box). The bees were then left for a 2 day acclimation period. During the acclimation period—any dead bees from the initial collection process were replaced with newly captured bees. At the end of the 2 days, only boxes in which the honeybees consumed the sucrose solution were included in the trial.

Treatment Groups

Untreated Infected (Control): Fed 66% w/v sucrose solution then infected with U.S. *Nosema* Ceranae (>100,000 per bee), on study day 5. The bees were subsequently fed 50 microliter per bee 66% sucrose solution for another 12-14 days.

Treatment group (all four ATP/ADP transporter dsRNA sequences): Fed regular 66% w/v sucrose solution then infected with U.S. *Nosema ceranae* (>100,000 per bee), either 10 days or 3 days after acclimation. The bees were subsequently fed 50 microliter per bee 66% sucrose solution for another 12-14 days, containing 20 ug/ml of each of 4 *Nosema* ATP/ADP transporter sequence dsRNA (complementary to sequences as set forth in SEQ ID NOs. 56-59, Evaluation Methods Visual Inspection—Survival Rate at the End of the Experiment Following administration of treatment solutions to bees' boxes at study day 3, each day the bees in each box are visually inspected and the number of dead bees counted in each box.

Hunger Levels—Proboscis Extension Response

Bees infected with *Nosema* show increased hunger level that is typified by increased responsiveness to sugar. Specifically, bees infected with *Nosema* show a lower threshold level of responsiveness to sugar in a Proboscis Extension Reflex assay.

At the end of the feeding regimen in the boxes or mini-hives, bees were placed for 5 minutes in a freezer, captured individually and individually placed in a glass vial and chilled on ice until immobile. Then they were strapped within a 4.5 cm long plastic drinking straw with a small strip of tape on the thorax. Testing begins 45 minutes after the last bee is strapped to allow the bees to get acclimated and 24 bees are tested at a time. The antennae of a strapped bee was touched with a droplet of sucrose and proboscis extension response [response is full extension of the proboscis—a Proboscis Extension Response (PER)]—is recorded. Each bee is assayed for PER with a concentration series of 0.1%, 0.3%, 1%, 3%, 10%, and 30% sucrose solution by weight. In between every two successive concentrations, the antennae are touched with water to control for possible sensitization from repeated stimulation.

*Nosema* Spore Counts

Each day, all the dead bees were removed from each box, pooled according to treatment and total *nosema* spore counts were performed with 100 microliter water per crushed bee. *Nosema* counts were performed essentially as described previously by Cantwell et al: Briefly, bee abdomens were ground with a glass pestle, vigorously mixed with 1.5-2.0 ml water, and sampled (10 μl) into a hemacytometer for counting. Total number of *Nosema* under the microscope were counted for 16 small squares (or one large square). The average *Nosema* spore count per bee was calculated as follows:

(total number of spores counted)(4,000,000)/number of squares counted=number of spores per bee.

dsRNA Preparation:

*Nosema* sequences corresponding to mitosomal and non-mitosomal proteins associated with energy metabolism and ATP/ADP transport (SEQ ID NOs: 27, 44, 45, 46 and 47) were cloned into a plasmid between two opposing T7 promoters. Following propagation of plasmid DNA, the viral fragments, including the T7 promoters, were excised, gel-purified, and served as templates for T7-directed in-vitro transcription.

Real Time PCR

Preparation of Samples:

Only live bees were collected, to a 15 ml collection tube. The tubes were frozen immediately in liquid nitrogen and transferred to −70 c. Standard curves were generated for each reaction, specific curves for each gene. The standard curves were based on known concentration of plasmids suspensions, cloned with the fragments amplified by each tested gene specific primers. The standard curves allow the calculation of the relative arbitrary number of mRNA copies from each tested gene.

The relative expression levels for each gene were calculated as the number of arbitrary copies of the tested gene in each sample divided by the arbitrary mRNA arbitrary copy number of a *Nosema ceranae* housekeeping gene (e.g. tubulin or actin). Mean and standard error values were calculated for each sample and sets of repeats, according to the experimental design.

Values of each treatment were featured as the relative expression from the control treatment at study day 0, and are given the 100% expression level. Mean and standard error values were calculated for each sample and sets of repeats, according to the experiment design, and standard statistics analysis. The desired fragments were reverse transcribed and amplified from RNA isolates of *Nosema*-infected bees. The pLUG plasmids were generated using the pLUG(R)-Multi TA cloning vector kit from iNTRON Biotechnology (Gyeonggi-do, Korea), according to the manufacturer's protocol. The RT amplified fragments were ligated into the plasmids and the ligated plasmids transformed into Top10 *E. coli* competent cells, using heat shock transformation. The Top10 competent cells were incubated on LB agar plates containing 200 ug/ml Ampicillin and blue/white selection reagent. Colonies that grew and were positive were tested for presence of the insert using PCR amplification with the forward primer from the desired insert and the reverse primer from the pLUG plasmid. Positive colonies were grown in LB medium supplemented with 200 ug\ml ampicillin. The pLUG plasmids were purified from the top 10 *E. Coli* cells, using the IBI High speed plasmid mini kit (IBI Scientific, IOWA, USA), according to the manufacturer's protocol.

Real-Time PCR Protocol

1. RNA extraction from at least 3 stomachs of bees using peqGOLD Trifast, (Peqlab, Delaware, USA)
2. 8 ul of the RNA sample was removed and diluted to a total volume of 10 ul, for DNAse I treatment, 30 min in 37° C. (remainder stored at −70° c. for future use).
3. 2 µl of the DNAse-treated RNA was diluted to 1:5 and used as template for the RT PCR reaction.
4. AB HIGH CAPACITY cDNA RT KIT 200RXN+2× RNAse INHIBITOR (Applied Biosystems, California, USA, cat: 4374966) was used.
   The cDNA was diluted 1:5 to a final volume of 100 ml using Nuclease Free ddH2O and stored until use at −20° C.
5. During the qPCR reaction AB POWER SYBR GREEN PCR MIX 5 ML (Applied Biosystems, California, USA cat: 4367659) was used according to the following protocol:

| Component | Final Conc. | x1 Volume (µl) |
|---|---|---|
| Power SYBR Green PCR Master Mix (2X) | 1x | 7.5 |
| Forward Primer (10 uM) | 500 nm | 0.5 |
| Reverse Primer (10 uM) | 500 nm | 0.5 |
| Template | 1-100 ng | 2 |
| Water | | 4.5 |
| Total | | 15 |

Primers

| NAME | Target | Orientation | Sequence (SEQ ID NO) |
|---|---|---|---|
| B90111 | Honeybee Actin | Forward | AGGAATGGAAGCT TGCGGTA (SEQ ID NO: 11) |
| B90121 | Honeybee Actin | Reverse | AATTTTCATGGT GGATGGTGC (SEQ ID NO: 12) |
| Ntub7025 | Nosema C. Tubulin | Forward | AGAACCAGGAA CGATGGAGA (SEQ ID NO: 13) |
| Ntub7026 | Nosema C. Tubulin | Reverse | TCCTTGCAAACAAT CTGCAC (SEQ ID NO: 14) |
| NA70011 | Nc006 F | Forward | CACCTGAAAACAACT TACCTAC (SEQ ID NO: 15) |
| NA70021 | Nc006 R | Reverse | GTATCTTGCCTTAC CATCAC (SEQ ID NO: 16) |
| NA70031a | Nc123 F | Forward | GGaAAAGAtGAGAA TATGGAAGAAG (SEQ ID NO: 17) |
| NA70041b | Nc123 R | Reverse | CCAGTTACCCTTGT TTGTGTAGG (SEQ ID NO: 18) |

All reactions were carried out according to a thermal protocol consisting of 5 min at 95° C., then 40 cycles of the four-step protocol consisting of 94° C. 20 seconds, 60° C. 30 seconds, 72° C. 1 minute and 78° C. 20 seconds. Fluorescence was monitored repeatedly during the 78° C. step, in order to reduce fluorescence from primer artifacts.

Mini-Hive Experiments

Bees were introduced into minihives (~300 bees to each hive) at study day 0. Nurse bees were collected from within a honeybee colony that was previously checked and found to have no *N. ceranae*. The bees were transferred into every mini-hive containing a queen in a cage, approximately 300 bees in each mini-hive, 5 grams protein patty, and 5 grams candy.

The bees were observed during the first 2 days to determine stability in the minihives (i.e. no drastic changes in the population). At study day 3 daily feeding of sucrose syrup were initiated according to the treatment groups.

1. Untreated Infected: The bees were fed 15 ml per hive (50 µl per bee) per day 66% sucrose solution.
2. Treatment Group Bees were fed with 15 ml per hive (50 µl per bee) per day 66% sucrose solution supplemented with *Nosema* mitosomal and/or non-mitosomal dsRNA.

All mini-hives were monitored until egg laying by the queen is initiated. Only hives that accepted the new queen, take in the syrup treatments and have the queen initiate egg laying are included in the trial.

The mini-hive boxes are placed in a room kept at a constant temperature of 30° C., and in constant darkeness. The sucrose syrup with or without treatment is fed via a petri dish placed at the bottom of the mini-hive.

Following administration of treatment solutions to bees minihives at study day 3, each day the bees in each box were visually inspected to ensure the stability of the system. In all mini-hives, the queens layed eggs as required for inclusion criteria. At day 10, when the bees were infected with *Nosema ceranae* (approximately 100,000 spores per bee), once daily photographs were taken to record bee survival on both sides of each comb. The number of bees in each mini-hive was calculated by counting the bees on the screen from both sides of the single comb in the mini-hive.

Differential Effect of ATP/ADP Transporter dsRNA Sequences on Gene Real-Time PCR Transcript Levels Nurse bees were collected from a hive found to be without *N. ceranae*. Set up as described above.

Five treatment groups were defined, three hives of 30 bees per group—total 90 bees per group. Total of 15 minihives were included. Allocation to treatment groups was assigned arbitrarily on day 0. Daily feeding of 50 micoliters per bee 66% w/v sucrose solution with 1 microgram per bee each dsRNA of ATP/ADP transporters. Infection with *Nosema* was initiated on day 3. The five treatment groups were:

1. Control, Untreated, infected
2. Infected+NC006 dsRNA (complementary to SEQ ID NO: 56) only
3. Infected+NC123 dsRNA (complementary to SEQ ID NO: 57) only
4. Infected+NC006 dsRNA+NC123 dsRNA (complementary to SEQ ID NO: 56 and complementary to SEQ ID NO: 57)
5. Infected+dsRNA of each of all four ATP/ADP N.C. transporters (complementary to each of SEQ ID NOs: 56-59).

The plastic boxes were placed in a room kept at a constant temperature of 25° C., 70% RH and 12 hour light/dark cycle. Feeding was as described for the Bee Box protocol above.

Live bees were collected at day 0 and at day 13 after infection. From each box, bees were pooled into groups of 3 bees (3×3 pools per hive, total 9 samples from each treatment), and RNA was extracted separately for each group, as described above.

Example 1: *Nosema ceranae* Genome Homologues to ATP/ADP Transporter Proteins Found in *Encephalitozoon cuniculi*

The *N. ceranae* genome has been published. FIG. 1 shows a sequence alignment between the mitosomal and non-mitosomal ATP transporter proteins found in *Encephalitozoon cuniculi* and four homologues identified in *N. ceranae.*

Example 2: dsRNA Targeting *Nosema* Mitosomal and Non-Mitosomal ATP/ADP Transporter Homologues Reduces *Nosema* Spore Counts and Mortality Following Infection Since *Nosema* rarely reduces nurse bee lifespan in box experiments due to the feeding of the bees ad-libitum (not shown), indicators for reduced lifespan are best achieved in a hive setting. In our box experiments, no difference was observed in forager lifespan within the time span of the experiment. When bee lifespan was evaluated in the more natural mini-hive setting (FIG. 2), it was clearly evident that bees in untreated hives succumb earlier to *Nosema* infection in relation to bees from hives fed with dsRNA targeting 4 *Nosema* mitosomal and non-mitosomal ATP/ADP transporter homologues (NC123, NC006, NC014 and NC017).

In order to determine the effectiveness of feeding dsRNA in prevention of *Nosema*, parasite levels in dead bees from *Nosema* infected samples were determined. In all box and mini-hive experiments from 7 days post infection to 15 days post infection (bees in which no parasites were detected under the microscope were excluded), counting parasite levels clearly showed that the bees fed with dsRNA from the 4 *Nosema ceranae* ATP/ADP transporter homologues have an over three-fold lower count compared with untreated controls (FIG. 3) ($N=75$ samples $p<0.0001$).

Example 3: dsRNA Targeting *Nosema* Mitosomal and Non-Mitosomal ATP/ADP Transporter Homologues Reduces Hunger (Proboscis Extension Response) in Bees Infected with *Nosema Cerana*

In order to determine whether feeding *N. ceranae* mitosomal and non-mitosomal ATP/ADP-specific dsRNA reduces energetic stress in bees following *N. ceranae* infection, Proboscis Extension Reflex (PER), an indicator of hunger, was tested in treated and control bees.

Metabolic stress following *N. ceranae* infection in bees manifests in increased responsiveness to very low concentrations of sucrose, with the PER at low (<1%) sucrose being measurably increased in the infected bees. FIG. 4 shows that feeding *N. ceranae* mitosomal and non-mitosomal ATP/ADP-specific dsRNA increases the responsiveness threshold of the treated bees, compared to that of untreated bees. Although at higher (10-30%) sucrose concentration and at medium concentration of sucrose (1-3%) the discernible difference was not statistically significant, at the lower concentrations (0.1-0.3%), the difference in response was significant ($p<0.03$ N responses=330), indicating reduced metabolic stress (e.g. hunger) in the bees fed with the *N. ceranae* mitosomal and non-mitosomal ATP/ADP transporter orthologue-specific dsRNA. While not wishing to be limited to a single hypothesis, one explanation would be that silencing the *N. ceranae* mitosomal and non-mitosomal ATP/ADP transport homologues has a direct effect on energy drain caused by the *N. ceranae* infection (total responses=1000).

Further, when *Nosema* counts were performed on the treated and control bees participating in the bioassay (PER), no significant difference in the levels of parasite infestation in bees from the different groups was discernible (results not shown). While not wishing to be limited to a single hypothesis, one explanation of this would be that treatment of the bees with the *Nosema*-specific dsRNA not only acts to eliminate the parasite infestation, but weakens the virulence and/or metabolic load of the parasite infection, enhancing survival among even infected bees. This is further borne out by the observation that in the minihive experiments, untreated controls the bee population was found to decline by more than a third following infection with *Nosema*, and none of the live bees had apparent *Nosema*. Without being limited to one explanation, this could be due to a more rapid mortality of infected bees.

Example 4: dsRNA Targeting *Nosema* Mitosomal and Non-Mitosomal ATP/ADP Transporter Homologues Effectively Reduces Transcript Levels of the Targeted ATP/ADP Transporter Homologues In order to determine whether feeding bees dsRNA of *Nosema* mitosomal and non-mitosomal ATP/ADP transporter homologues results in a specific effect on expression of the targeted genes, and not in a generalized alteration of *Nosema* metabolism and/or gene expression, transcript levels of specific targeted genes in infected bees were evaluated by Real-Time PCR, and standardized against housekeeping gene expression (*Nosema* tubulin).

FIG. 5 illustrates the effect of feeding bees dsRNA of *Nosema* mitosomal and non-mitosomal ATP/ADP transporter homologues on the transcript levels of specific *Nosema* mitosomal proteins (Nc123, SEQ ID NO: 19). Feeding dsRNA of *Nosema* mitosomal ATP/ADP transporter homologue Nc006 ("NC006 Treatment") did not reduce the expression of *Nosema* mitosomal and non-mitosomal ATP/ADP transporter homologue Nc123. Feeding bees dsRNA of *Nosema* mitosomal ATP/ADP transporter homologue Nc123 (complementary to the sequence as set forth in SEQ ID NO: 57) alone ("NC123 Treatment"), or in combination with one ("NC6+NC123 Treatment") or more ("R.N. Treatment") other *Nosema* mitosomal and non-mitosomal ATP/ADP transporter homologues (Nc006, complementary to the sequence as set forth in SEQ ID NO: 56, Nc014, complementary to the sequence as set forth in SEQ ID NO: 58 and Nc017, complementary to the sequence as set forth in SEQ ID NO: 59) consistently resulted in specific silencing of 60-70% of *Nosema* mitosomal ATP/ADP transporter homologue Nc123 gene expression. Thus, silencing of *Nosema* genes by feeding bees with dsRNA of *Nosema* mitosomal and non-mitosomal proteins results in effective and transcript-specific silencing of the target *Nosema* gene expression.

Example 5: Synergic Enhancement of Survival Following *Nosema* Infection by Feeding dsRNA Targeting *Nosema* Mitosomal and Non-Mitosomal Proteins In order to determine the effect of silencing individual *Nosema* mitosomal and non-mitosomal energy-related homologues with dsRNA on bee resistance to *Nosema* infection, survival of bees in minihives following feeding with a variety of dsRNAs of *Nosema* mitosomal and non-mitosomal energy-related homologues was monitored.

FIG. 6 shows that feeding dsRNAs of some, but not all of the *Nosema* mitosomal and non-mitosomal energy-related homologues tested resulted in significantly enhanced survival of the treated bees following infection with *Nosema* [see, for example, "nc14" (complementary to the sequence as set forth in SEQ ID NO: 58) and "tom70" (complementary to the sequence as set forth in SEQ ID NO: 55) compared to "nc17" (complementary to the sequence as set forth in SEQ ID NO: 59) or "nc123" (complementary to the sequence as set forth in SEQ ID NO: 57)]. Feeding bees combined dsRNA of more than one *Nosema* mitosomal and non-mitosomal energy-related orthologue was also not always equally effective—dsRNA of combined *Nosema* mitosomal and non-mitosomal ATP/ADP transporter homologues and the mitosomal TOM-70 orthologue ("REN+tom70") was significantly more effective in enhancing survival than the *Nosema* mitosomal and non-mitosomal ATP/ADP transporter homologues alone ("REN"). FIG. 7 shows that the enhanced survival of bees fed with dsRNA of combined *Nosema* mitosomal and non-mitosomal ATP/ADP transporter homologues and the mitosomal TOM-70 orthologue ("REN+tom70") was significant for the entire duration of the study.

Feeding bees a combination of dsRNA of *Nosema* non-mitosomal ATP/ADP transporter homologues nc014 and nc017, and the mitosomal TOM-70 orthologue was effective in enhancing survival in minihive experiments (FIG. 8). Whereas the bee population fed sucrose only ("S.O.") declined more than a third by day 20 following infection, survival of bees fed the combined dsRNA for *Nosema* ATP/ADP transporter homologues nc014 and nc017 with dsRNA for *Nosema* TOM-70 ("TOM 70+NC14+NC17") remained high throughout the duration of the study.

Spore counts from live bees treated with combined dsRNA for *Nosema* ATP/ADP transporter homologues nc014 and nc017 with dsRNA for *Nosema* TOM-70 ("TOM 70+NC14+NC17") (FIG. 9) and live control bees ("S.O.") (FIG. 10) taken at completion of the minihive study (day 20) indicate near absence of *Nosema* infection in the live control bees, while high levels of *Nosema* infection were detected in the live bees fed dsRNA. While not wanting to be limited to a single hypothesis, this may be explained by the phenomenon of high susceptibility to mortality from *Nosema* infection in the untreated bees, leaving only uninfected bees alive in the hives, while in the bees fed the *Nosema* dsRNA, enhanced resistance to the effects of the parasite infection resulted in reduced mortality and greater survival among infected bees.

Resistance of the bees to *Nosema* infection was also tested by feeding dsRNAs of *Nosema* mitosomal and non-mitosomal energy-related homologues prior to infection with the parasite, and monitoring survival of the bees in box protocol (continuous feeding) following infection. FIG. 11 illustrates the superior survival, over more than 2 weeks, of bees fed dsRNA of combined *Nosema* mitosomal and non-mitosomal ATP/ADP transporter homologues (nc123, nc006, nc014 and nc017) and the mitosomal TOM-70 orthologue (REN+TOM 70, "Treatment C"), compared to infected ("Treatment B") bees, and even to uninfected bees ("Treatment A") bees fed sucrose only.

Thus, the results brought herein clearly indicate that gene silencing by feeding bees dsRNA of some, but not all *Nosema* mitosomal and non-mitosomal proteins associated with energy metabolism such as ATP/ADP transporter and TOM-70 homologues, can effectively reduce *Nosema* infection and virulence, enhancing overall survival, and specifically enhancing survival of *Nosema*-infected bees.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

CITED REFERENCES

Akiyoshi et al., 2009 *PloS Patholog;* 5:1000261
Burri et al. 2006 *PNAS;* 103:15916-20
Chen et al 2009 *Genome Biol Evol.* 2009:165-75
Cornman, R. S. et al, 2009, *PLoS Pathogens* 5(6)
Gill and Fast, 2007 *BMC Mol. Biol;* 8:24
Katinka et al., 2001 *Nature;* 414:450-53
Malhota et al 2002 *Mol. Microbiol.* 45:1245-54
Maori et al. 2009 *Insect Mol Biol* 18:5-60
Mayack and Daug 2009 *J. Invertebr Pathol.* 100(3):185-8
Nakayashiki, et al. 2006 *Mol Evol* 63:127-135
Peyretaillade et al, 1998, *NAR;* 26:3513-20
Price and Gatehouse 2008. *Trends in Biotechnology* 26:393-400
Siomi H and Siomi M 2009. *Nature* 457:396-404
Slamovits et al. 2004 *Curr Biol;* 14:891-96.
Taylor et al 2008 *Biochem J.* 409:563-69
Tsaousis et al. *Nature* 453, 553-556;
Ulla et al. 2004 *Cellular Microb.* 6:509-19
vanEngelsdorp et al. *PLoS* August 2009
Williams et al., 2008 *BMC Genomics;* 9:200;

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09932579B2). An electronic copy of the "Sequence Listing" will also be available from the USPTO upon request and payment of the fee set forth in 37 CFR 1.19(b)(3).

What is claimed is:

1. A method for reducing the susceptibility of a bee or increasing the survival rate of a bee colony to a *Nosema ceranae* infection, the method comprising feeding a bee of the bee colony an effective amount of an isolated nucleic acid agent comprising a nucleic acid sequence of at least 19 contiguous nucleotides capable of binding through complementary base pairing to an mRNA encoding a *Nosema ceranae* polypeptide, wherein the *Nosema ceranae* polypeptide is selected from the group consisting of Nc014 and Nc017, and wherein expression of the mRNA encoding the *Nosema ceranae* polypeptide is downregulated, thereby reducing the susceptibility of said bee or increasing the survival rate of said bee colony to said *Nosema ceranae* infection.

2. The method of claim 1, wherein said bee is a honeybee.

3. The method of claim 2, wherein said honeybee is a forager.

4. The method of claim 2, wherein said honeybee is a hive bee.

5. The method of claim 1, wherein said nucleic acid agent comprises a nucleic acid sequence of at least 19 contiguous nucleotides complementary to any of the sequences as set forth in the group consisting of SEQ ID NOs: 46, 47, 58, and 59.

6. The method of claim 1, wherein said nucleic acid agent comprises a plurality of nucleic acid sequences of at least 19 contiguous nucleotides complementary to any of the sequences as set forth in the group consisting of SEQ ID NOs: 58 and 59.

7. The method of claim 1, wherein said feeding comprises providing a liquid bee-ingestible composition.

8. The methods of claim 1, wherein said feeding comprises providing a solid bee-ingestible composition.

9. A method for reducing the susceptibility of a bee or increasing the Survival rate of a bee colony to a *Nosema ceranae* infection, the method comprising feeding a bee of the bee colony an effective amount of a nucleic acid agent comprising at least two non-contiguous nucleic acid sequences capable of binding through complementary base pairing to an mRNA encoding a *Nosema ceranae* polypeptide, wherein said nucleic acid sequences comprise at least one nucleic acid sequence of at least 19 contiguous nucleotides complementary to the sequence as set forth in SEQ ID NO: 59 and at least one nucleic acid sequence of at least 19 contiguous nucleotides complementary to the sequence as set forth in SEQ ID NOs: 57 or 58, and wherein expression of the mRNA encoding a *Nosema ceranae* polypeptide is downregulated, thereby reducing the susceptibility of said bee or increasing the survivability increasing the survival rate of said bee colony to said *Nosema ceranae* infection.

10. A method for reducing the susceptibility of a bee or increasing the survival rate of a bee colony to a *Nosema ceranae* infection, the method comprising feeding a bee of the bee colony an effective amount of a nucleic acid agent comprising at least two non-contiguous nucleic acid sequences capable of binding through complementary base pairing to an mRNA encoding a *Nosema ceranae* polypeptide, wherein said nucleic acid sequences comprise a plurality of nucleic acid sequences comprising at least one nucleic acid sequence of at least 19 contiguous nucleotides complementary to a sequence selected from the group consisting of SEQ ID NOs: 58 and 59, and wherein expression of the mRNA encoding a *Nosema ceranae* polypeptide is downregulated, thereby reducing the susceptibility of said bee or increasing the survival rate of said bee colony to said *Nosema ceranae* infection.

11. A method of reducing the susceptibility of a bee or increasing the survival rate of a bee colony to a *Nosema ceranae* infection, the method comprising feeding a bee of the bee colony an effective amount of double stranded ribonucleic nucleic acid (dsRNA), said dsRNA comprising at least one sequence complementary to at least 21 nucleotides of a *Nosema ceranae*-specific mRNA encoding a *Nosema ceranae* polypeptide, wherein the *Nosema ceranae* polypeptide is selected from the group consisting of Nc014 and Nc017, and wherein the dsRNA is capable of inducing degradation of said *Nosema ceranae*-specific mRNA.

* * * * *